United States Patent
Defauw et al.

(10) Patent No.: US 12,304,903 B2
(45) Date of Patent: *May 20, 2025

(54) PROCESS FOR MAKING AN ISOXAZOLINE COMPOUND AND INTERMEDIATE THEREOF

(71) Applicant: Elanco US Inc., Greenfield, IN (US)

(72) Inventors: Jean Marie Defauw, Greenfield, IN (US); Guanmin Wu, Greenfield, IN (US); Jingdan Hu, Greenfield, IN (US); Jing Chen, Greenfield, IN (US); Xin Zhang, Greenfield, IN (US); Ping Huang, Greenfield, IN (US)

(73) Assignee: Elanco US Inc., Greenfield, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/978,995

(22) Filed: Dec. 12, 2024

(65) Prior Publication Data

US 2025/0109125 A1    Apr. 3, 2025

Related U.S. Application Data

(63) Continuation of application No. 18/006,277, filed as application No. PCT/US2021/042769 on Jul. 22, 2021.

(60) Provisional application No. 63/055,923, filed on Jul. 24, 2020.

(30) Foreign Application Priority Data

Jul. 24, 2020   (WO) ............... PCT/CN2020/104035

(51) Int. Cl.
C07D 413/04    (2006.01)

(52) U.S. Cl.
CPC ................... C07D 413/04 (2013.01)

(58) Field of Classification Search
CPC .................................................. C07D 413/04
USPC ....................................................... 548/242
See application file for complete search history.

(56) References Cited

U.S. PATENT DOCUMENTS

| | | | |
|---|---|---|---|
| 1,072,244 A | 9/1913 | Lynch |
| 8,383,659 B2 | 2/2013 | Nanchen |
| 8,410,153 B2 | 4/2013 | Lahm |
| 8,415,310 B2 | 4/2013 | Vaillancourt |
| 8,466,115 B2 | 6/2013 | Curtis |
| 8,618,126 B2 | 12/2013 | Le Hir De Fallois |
| 8,642,636 B2 | 2/2014 | Meng |
| 8,735,362 B2 | 5/2014 | Cassayre |
| 8,754,053 B2 | 6/2014 | Pitterna |
| 8,895,587 B2 | 11/2014 | Cassayre |
| 8,957,058 B2 | 2/2015 | Cassayre |
| 8,980,893 B2 | 3/2015 | Le Hir De Fallois |
| 9,061,013 B2 | 6/2015 | Vaillancourt |
| 9,066,945 B2 | 6/2015 | Turberg |
| 9,073,912 B2 | 7/2015 | Sheehan |
| 9,078,444 B2 | 7/2015 | Cassayre |
| 9,133,172 B2 | 9/2015 | Chubb |
| 9,173,870 B2 | 11/2015 | Fuchs |
| 9,180,121 B2 | 11/2015 | Soll |
| 9,204,648 B2 | 12/2015 | Cassayre |
| 9,226,928 B2 | 1/2016 | Chubb |
| 9,233,100 B2 | 1/2016 | Soll |
| 9,259,417 B2 | 2/2016 | Soll |
| 9,307,766 B2 | 4/2016 | Cassayre |
| 9,339,505 B2 | 5/2016 | Cassayre |
| 9,376,434 B2 | 6/2016 | Le Hir De Fallois |
| 9,532,978 B2 | 1/2017 | Fuchs |
| 9,533,961 B2 | 1/2017 | Fischer et al. |
| 9,545,106 B2 | 1/2017 | Cassayre et al. |
| 9,550,739 B2 | 1/2017 | Fischer et al. |
| 9,593,126 B2 | 3/2017 | Greenwood et al. |

(Continued)

FOREIGN PATENT DOCUMENTS

| | | |
|---|---|---|
| EP | 1538138 A1 | 6/2005 |
| KR | 2021005334 | 4/2021 |

(Continued)

OTHER PUBLICATIONS

Kazutaka et al., "Enatioselective Syntesis of Trifluromethyl-Substituted 2-Isoxazolines: Asymmetric Hydroxylamine/Enome Cascade Reaction**", Angew. Chem. Int. Ed., 2010, pp. 5762-5766, vol. 49. 2010.

(Continued)

*Primary Examiner* — Taylor V Oh

(74) *Attorney, Agent, or Firm* — McBee Moore & Vanik IP, LLC

(57) ABSTRACT

The present disclosure provides processes for making enantiomerically pure isoxazoline compounds of formula (1),

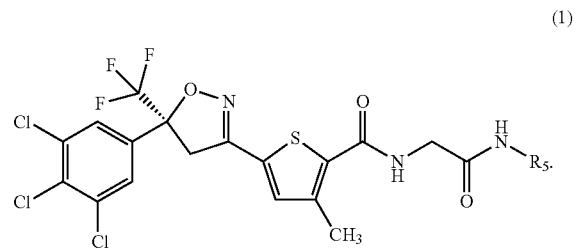

(1)

The present disclosure also provides processes for making enantiomerically pure isoxazoline compounds of formula (1) characterized by improving the enantiomeric purity of 3-methyl-5-[(5S)-5-(3,4,5-trichlorophenyl)-5-(trifluoromethyl)-4H-isoxazol-3-yl]thiophene-2-carboxylic acid by crystallization.

28 Claims, No Drawings

(56) References Cited

U.S. PATENT DOCUMENTS

| | | |
|---|---|---|
| 9,598,389 B2 | 3/2017 | Lu et al. |
| 9,609,869 B2 | 4/2017 | Cassayre et al. |
| 9,655,884 B2 | 5/2017 | Williams et al. |
| 9,675,073 B2 | 6/2017 | Rawal et al. |
| 9,682,949 B2 | 6/2017 | Cassayre et al. |
| 9,686,988 B2 | 6/2017 | Rawal et al. |
| 9,714,228 B2 | 7/2017 | Qacemi et al. |
| 9,770,440 B2 | 9/2017 | Freehauf et al. |
| 9,776,994 B2 | 10/2017 | Lu et al. |
| 9,776,999 B2 | 10/2017 | Fallois et al. |
| 9,877,950 B2 | 1/2018 | Soll et al. |
| 9,913,471 B2 | 3/2018 | Cassayre et al. |
| 9,931,320 B2 | 4/2018 | Soll et al. |
| 10,155,730 B2 | 12/2018 | Pitterna |
| 10,206,400 B2 | 2/2019 | Cassayre |
| 10,212,936 B2 | 2/2019 | Renga |
| 10,266,524 B2 | 4/2019 | Cassayre |
| 10,272,071 B2 | 4/2019 | Heckeroth |
| 10,287,281 B2 | 5/2019 | Lu |
| 10,321,683 B2 | 6/2019 | Kagami |
| 10,350,196 B2 | 7/2019 | Foster |
| 10,383,854 B2 | 8/2019 | Soll |
| 10,433,552 B2 | 10/2019 | Yang |
| 10,456,358 B2 | 10/2019 | Lehay |
| 10,517,294 B2 | 12/2019 | El Qacemi |
| 10,537,549 B2 | 1/2020 | Tahtaoui |
| 10,561,641 B2 | 2/2020 | Cady |
| 10,596,156 B2 | 3/2020 | Soll |
| 10,653,675 B2 | 5/2020 | Heckeroth |
| 10,662,163 B2 | 5/2020 | Gorter De Vries |
| 10,710,991 B2 | 7/2020 | Cassayre |
| 10,722,448 B2 | 7/2020 | Hansen |
| 10,750,744 B2 | 8/2020 | Yang |
| 10,750,745 B2 | 8/2020 | Cassayre |
| 10,786,487 B2 | 9/2020 | Soll |
| 10,799,483 B2 | 9/2020 | Soll |
| 10,864,195 B2 | 12/2020 | Fuchs |
| 10,869,477 B2 | 12/2020 | Cassayre |
| 10,894,783 B2 | 1/2021 | Zhang |
| 10,973,759 B2 | 4/2021 | Kluger |
| 11,179,372 B2 | 11/2021 | Flochlay-Sigognault |
| 11,285,101 B2 | 3/2022 | Alteheld |
| 11,324,220 B2 | 5/2022 | Yang |
| 11,337,917 B2 | 5/2022 | Roepke |
| 11,357,231 B2 | 6/2022 | Cassayre |
| 11,484,528 B2 | 11/2022 | Cady et al. |
| 11,497,732 B2 | 11/2022 | Le Hir De Fallois |
| 11,505,548 B2 | 11/2022 | Hawryluk |
| 11,530,187 B2 | 12/2022 | Schmitt |
| 11,548,859 B2 | 1/2023 | Schmitt |
| 11,648,238 B2 | 5/2023 | Freehauf |
| 2010/0254959 A1 | 10/2010 | Lahm |
| 2011/0059988 A1 | 3/2011 | Heckeroth |
| 2011/0152312 A1 | 6/2011 | Le Hir De Fallois |
| 2011/0245157 A1 | 10/2011 | Meng |
| 2012/0023226 A1 | 1/2012 | Petersen |
| 2012/0035122 A1 | 2/2012 | Vaillancourt |
| 2012/0077765 A1 | 2/2012 | Vaillancourt |
| 2012/0238517 A1 | 9/2012 | Cassayre |
| 2012/0316124 A1 | 12/2012 | Pitterna |
| 2012/0329769 A1 | 12/2012 | El Qacemi |
| 2013/0065846 A1 | 3/2013 | Soll |
| 2013/0085064 A1 | 4/2013 | Hoegger |
| 2013/0210623 A1 | 8/2013 | Cassayre |
| 2013/0274302 A1 | 10/2013 | Fuchs |
| 2013/0281501 A1 | 10/2013 | Fuchs |
| 2014/0011758 A1 | 1/2014 | Vaillancourt |
| 2014/0019437 A1 | 1/2014 | Hays |
| 2014/0106633 A1 | 4/2014 | Koga |
| 2014/0107056 A1 | 4/2014 | Cassayre |
| 2014/0107057 A1 | 4/2014 | Cassayre |
| 2014/0107161 A1 | 4/2014 | Cassayre |
| 2014/0128358 A1 | 5/2014 | Cassayre |
| 2014/0179623 A1 | 6/2014 | Turberg |
| 2014/0228577 A1 | 8/2014 | Cassayre |
| 2014/0235533 A1 | 8/2014 | Smejkai |
| 2014/0235869 A1 | 8/2014 | Cassayre |
| 2014/0243375 A1 | 8/2014 | El Qacemi |
| 2014/0315794 A1 | 10/2014 | Le Hir De Fallois |
| 2014/0350261 A1 | 11/2014 | Toyama |
| 2014/0378415 A1 | 12/2014 | Cassayre |
| 2015/0011596 A1 | 1/2015 | Fuchs |
| 2015/0032046 A1 | 1/2015 | Deborski |
| 2015/0038440 A1 | 2/2015 | Chubb |
| 2015/0057239 A1 | 2/2015 | Freehauf |
| 2015/0111936 A1 | 4/2015 | Heckeroth |
| 2015/0119377 A1 | 4/2015 | Sheehan |
| 2015/0164864 A1 | 6/2015 | Soll |
| 2015/0183785 A1 | 7/2015 | Le Hir De Fallois |
| 2015/0209355 A1 | 7/2015 | Chubb |
| 2015/0223463 A1 | 8/2015 | Wendt |
| 2015/0272120 A1 | 10/2015 | El Qacemi |
| 2015/0291612 A1 | 10/2015 | Greenwood |
| 2015/0353532 A1 | 12/2015 | Lu |
| 2016/0015689 A1 | 1/2016 | Fuchs |
| 2016/0016927 A1 | 1/2016 | Lu |
| 2016/0024026 A1 | 1/2016 | Fischer |
| 2016/0024027 A1 | 1/2016 | Fischer |
| 2016/0051519 A1 | 2/2016 | Soll |
| 2016/0052907 A1 | 2/2016 | Cassayre |
| 2016/0235720 A1 | 8/2016 | Foster |
| 2016/0256442 A1 | 9/2016 | Cady |
| 2016/0286808 A1 | 10/2016 | Rawal |
| 2016/0296499 A1 | 10/2016 | Wendt |
| 2016/0303086 A1 | 10/2016 | Williams |
| 2016/0317439 A1 | 11/2016 | Lehay |
| 2016/0317502 A1 | 11/2016 | Heckeroth |
| 2016/0332975 A1 | 11/2016 | Heckeroth |
| 2016/0368883 A1 | 12/2016 | Pitterna |
| 2016/0374994 A1 | 12/2016 | Soll |
| 2017/0020849 A1 | 1/2017 | Soll |
| 2017/0022197 A1 | 1/2017 | Le Hir De Fallois |
| 2017/0071207 A1 | 3/2017 | Cassayre |
| 2017/0135347 A1 | 5/2017 | Kagami |
| 2017/0152250 A1 | 6/2017 | Cassayre |
| 2017/0157040 A1 | 6/2017 | Kluger |
| 2017/0239218 A1 | 8/2017 | Le Hir De Fallois |
| 2017/0247361 A1 | 8/2017 | Cassayre |
| 2017/0283405 A1 | 10/2017 | Lu |
| 2017/0290766 A1 | 10/2017 | Alteheld |
| 2017/0311601 A1 | 11/2017 | Yang |
| 2017/0348286 A1 | 12/2017 | Williams |
| 2017/0354593 A1 | 12/2017 | Majumdar |
| 2017/0360045 A1 | 12/2017 | Renga |
| 2018/0085352 A1 | 3/2018 | Fuchs |
| 2018/0153170 A1 | 6/2018 | Cassayre |
| 2018/0155301 A1 | 6/2018 | Heckeroth |
| 2018/0169073 A1 | 6/2018 | Flochlay-Sigognault |
| 2018/0263905 A1 | 9/2018 | Kluger |
| 2018/0354917 A1 | 12/2018 | Gorter De Vries |
| 2019/0071407 A1 | 3/2019 | Pitterna |
| 2019/0091133 A1 | 3/2019 | Hansen |
| 2019/0105305 A1 | 4/2019 | Soll |
| 2019/0133129 A1 | 5/2019 | Yang |
| 2019/0142795 A1 | 5/2019 | Tahtaoui |
| 2019/0166842 A1 | 6/2019 | Cassayre |
| 2019/0192486 A1 | 6/2019 | Heckeroth |
| 2019/0201332 A1 | 7/2019 | Alteheld |
| 2019/0216784 A1 | 7/2019 | Soll |
| 2019/0315728 A1 | 10/2019 | Cassayre |
| 2019/0336442 A1 | 11/2019 | Kluger |
| 2019/0343808 A1 | 11/2019 | Flochlay-Sigognault |
| 2019/0375725 A1 | 12/2019 | Zhang |
| 2020/0000720 A1 | 1/2020 | Lehay |
| 2020/0022959 A1 | 1/2020 | Cady |
| 2020/0038333 A1 | 2/2020 | Hirama |
| 2020/0038370 A1 | 2/2020 | Le Hir De Fallois |
| 2020/0331867 A1 | 10/2020 | Schenck |
| 2020/0339559 A1 | 10/2020 | Hawryluk |
| 2020/0390688 A1 | 12/2020 | Hepler |
| 2020/0390748 A1 | 12/2020 | Sheehan |
| 2020/0405692 A1 | 12/2020 | Williams |
| 2021/0022344 A1 | 1/2021 | Yang |
| 2021/0061775 A1 | 3/2021 | Heckeroth |

(56) References Cited

U.S. PATENT DOCUMENTS

| | | |
|---|---|---|
| 2021/0087164 A1 | 3/2021 | Zhang |
| 2021/0161867 A1 | 6/2021 | Freehauf |
| 2021/0177749 A1 | 6/2021 | Freehauf |
| 2021/0177808 A1 | 6/2021 | Freehauf |
| 2021/0220360 A1 | 7/2021 | Kolhe |
| 2021/0236420 A1 | 8/2021 | Kluger |
| 2021/0299104 A1 | 9/2021 | Cady |
| 2021/0353537 A1 | 11/2021 | Lehay |
| 2021/0354283 A1 | 11/2021 | Flochlay-Sigognault |
| 2021/0379023 A1 | 12/2021 | De Rose |
| 2022/0046921 A1 | 2/2022 | Nakamura |
| 2022/0048874 A1 | 2/2022 | Schmitt |
| 2022/0073479 A1 | 3/2022 | Schmitt |
| 2022/0142984 A1 | 5/2022 | Alteheld |
| 2022/0201983 A1 | 6/2022 | Allan |
| 2022/0259176 A1 | 8/2022 | Zhang |
| 2022/0296564 A1 | 9/2022 | Valle Colon |
| 2022/0323421 A1 | 10/2022 | Northrup |
| 2022/0323472 A1 | 10/2022 | Spallitta |
| 2023/0000082 A1 | 1/2023 | Cassayre |
| 2023/0087923 A1 | 3/2023 | Soll |
| 2023/0095926 A1 | 3/2023 | O'Neill |
| 2023/0146944 A1 | 5/2023 | Hawryluk |
| 2023/0157288 A1 | 5/2023 | Sakanishi |
| 2023/0233530 A1 | 7/2023 | Freehauf |
| 2024/0308993 A1 | 9/2024 | Hu |

FOREIGN PATENT DOCUMENTS

| | | |
|---|---|---|
| TW | 201739740 A | 11/2017 |
| WO | 2004006906 A2 | 1/2004 |
| WO | 2004018410 A1 | 3/2004 |
| WO | 2007075459 A2 | 7/2007 |
| WO | 2009002809 A2 | 12/2008 |
| WO | 2009024541 A2 | 2/2009 |
| WO | 2010059719 A2 | 5/2010 |
| WO | 2010070068 A2 | 6/2010 |
| WO | 2011067272 A1 | 6/2011 |
| WO | 2011075591 A1 | 6/2011 |
| WO | 2011101229 A1 | 8/2011 |
| WO | 2011101402 A1 | 8/2011 |
| WO | 2011104087 A1 | 9/2011 |
| WO | 2011104089 A1 | 9/2011 |
| WO | 2011154433 A2 | 12/2011 |
| WO | 2012017359 A1 | 2/2012 |
| WO | 2012038851 A1 | 3/2012 |
| WO | 2012045700 A1 | 4/2012 |
| WO | 2012049327 A2 | 4/2012 |
| WO | 2012084852 A2 | 6/2012 |
| WO | 2012086923 A1 | 6/2012 |
| WO | 2012089622 A2 | 7/2012 |
| WO | 2012120399 A1 | 9/2012 |
| WO | 2012127347 A1 | 9/2012 |
| WO | 2012156400 A1 | 11/2012 |
| WO | 2012163948 A1 | 12/2012 |
| WO | 2012163959 A1 | 12/2012 |
| WO | 2013026726 A1 | 2/2013 |
| WO | 2013026929 A1 | 2/2013 |
| WO | 2013026930 A1 | 2/2013 |
| WO | 2013026933 A1 | 2/2013 |
| WO | 2013037626 A1 | 3/2013 |
| WO | 2013039948 A1 | 3/2013 |
| WO | 2013050302 A1 | 4/2013 |
| WO | 2013079407 A1 | 6/2013 |
| WO | 2013092942 A1 | 6/2013 |
| WO | 2013116230 A1 | 8/2013 |
| WO | 2013116236 A1 | 8/2013 |
| WO | 2013119442 A1 | 8/2013 |
| WO | 2013135674 A1 | 9/2013 |
| WO | 2013150055 A1 | 10/2013 |
| WO | 2013169622 A1 | 11/2013 |
| WO | 2014001120 A1 | 1/2014 |
| WO | 2014039422 A1 | 3/2014 |
| WO | 2014039475 A1 | 3/2014 |
| WO | 2014053555 A1 | 4/2014 |
| WO | 2014072480 A1 | 5/2014 |
| WO | 2014079825 A1 | 5/2014 |
| WO | 2014079935 A1 | 5/2014 |
| WO | 2014079937 A1 | 5/2014 |
| WO | 2014079941 A1 | 5/2014 |
| WO | 2014081800 A1 | 5/2014 |
| WO | 2014090918 A1 | 6/2014 |
| WO | 2014114250 A1 | 7/2014 |
| WO | 2014135095 A1 | 9/2014 |
| WO | 2014172871 A1 | 10/2014 |
| WO | 2014189837 A1 | 11/2014 |
| WO | 2015048371 A1 | 4/2015 |
| WO | 2015055497 A1 | 4/2015 |
| WO | 2015066162 A1 | 5/2015 |
| WO | 2015086551 A1 | 6/2015 |
| WO | 2015091898 A1 | 6/2015 |
| WO | 2015091900 A1 | 6/2015 |
| WO | 2015100232 A2 | 7/2015 |
| WO | 2015132592 A1 | 9/2015 |
| WO | 2015169723 A1 | 9/2015 |
| WO | 2016002790 A1 | 1/2016 |
| WO | 2016018872 A1 | 2/2016 |
| WO | 2016018875 A1 | 2/2016 |
| WO | 2016073347 A1 | 5/2016 |
| WO | 2016099929 A1 | 6/2016 |
| WO | 2016102437 A1 | 6/2016 |
| WO | 2016138339 A1 | 9/2016 |
| WO | 2016164487 A1 | 10/2016 |
| WO | 2016207234 A1 | 12/2016 |
| WO | 2017083326 A1 | 5/2017 |
| WO | 2017147352 A1 | 8/2017 |
| WO | 2017176948 A1 | 10/2017 |
| WO | 2017196607 A1 | 11/2017 |
| WO | 2018039508 A1 | 3/2018 |
| WO | 2018187623 A1 | 10/2018 |
| WO | 2019091936 A1 | 5/2019 |
| WO | 2019091940 A1 | 5/2019 |
| WO | 2019115492 A1 | 5/2019 |
| WO | 2019122324 A1 | 6/2019 |
| WO | 2019236274 A1 | 12/2019 |
| WO | 2020051106 A1 | 3/2020 |
| WO | 2020054835 A1 | 3/2020 |
| WO | 2020127878 A1 | 6/2020 |
| WO | 2020127935 A1 | 6/2020 |
| WO | 2020219871 A1 | 10/2020 |
| WO | 2020225143 A1 | 11/2020 |
| WO | 2020252269 A1 | 12/2020 |
| WO | 2021013825 A1 | 1/2021 |
| WO | 2021122513 A1 | 6/2021 |
| WO | 2021122515 A1 | 6/2021 |
| WO | 2021122521 A1 | 6/2021 |
| WO | 2021200488 A1 | 10/2021 |
| WO | 2021233967 A1 | 11/2021 |
| WO | 2021241898 A1 | 12/2021 |
| WO | 2022049149 A1 | 3/2022 |
| WO | 2022051478 A1 | 3/2022 |
| WO | 2022087326 A1 | 4/2022 |
| WO | 2022140728 A1 | 6/2022 |
| WO | 2022155352 A1 | 7/2022 |
| WO | 2022173727 A1 | 8/2022 |
| WO | 2022212399 A1 | 10/2022 |
| WO | 2022258797 A1 | 12/2022 |
| WO | 2022269042 A1 | 12/2022 |
| WO | 2023018806 A1 | 2/2023 |

OTHER PUBLICATIONS

International Search Report of International Patent Application No. PCT/US2021/042769, mailed Nov. 10, 2021. 2021.

PROCESS FOR MAKING AN ISOXAZOLINE COMPOUND AND INTERMEDIATE THEREOF

CROSS-REFERENCE TO RELATED APPLICATIONS

This application is a Track One Continuation of U.S. application Ser. No. 18/006,277, filed 20 Jan. 2023, which is the National Stage entry of International Application No. PCT/US21/42769, filed 22 Jul. 2021, which claims priority to U.S. Application No. 63/055,923, filed 24 Jul. 2020 and to Chinese Application No. PCT/CN2020/104035, filed 24 Jul. 2020, the entire contents of each of which are incorporated herein by reference.

BACKGROUND

Field

Lotilaner, 5-[(5S)-4,5-dihydro-5-(3,4,5-trichlorophenyl)-5-(trifluoromethyl)-3-isoxazolyl]-3-methyl-N-[2-oxo-2-[(2,2,2-trifluoroethyl)amino]ethyl]-2-thiophenecarboxamide, also known as (S)-5-[5-(3,4,5-trichlorophenyl)-5-trifluoromethyl-4,5-dihydro-isoxazol-3-yl]-3-methyl-thiophene-2-carboxylic acid [(2,2,2-trifluoro-ethylcarbamoyl)-methyl]-amide, is the compound of formula (1a) shown below:

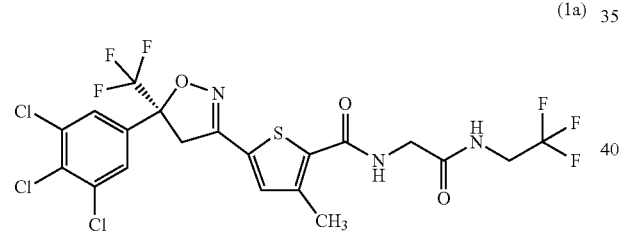

(1a)

and is useful in pest control, in particular in the control of ectoparasites. Lotilaner inhibits insect and acarine gamma-aminobutyric acid (GABA)-gated chloride channels. This inhibition blocks the transfer of chloride ions across cell membranes, which results in the death of insects and acarines. In particular, lotilaner is useful in the treatment of ectoparasites, such as flea infestations and the treatment and control of tick infestations in animals including humans, farm animals including fish, and domestic animals, especially in dogs.

DESCRIPTION OF RELATED ART

Lotilaner belongs to the well-known class of isoxazoline derivatives which have insecticidal and acaricidal activity and can be used in agriculture, forestry, turf, household, wood products, nursery crops protection, and veterinary fields. For example such isoxazolines are disclosed in WO 2010/070068 and WO2013/079407.

Manufacture of pure enantiomers is expensive and time-consuming. A method for the preparation of lotilaner is described in WO 2014/090918 in which the (S)-enantiomer is prepared by resolution of the carboxylic acid below:

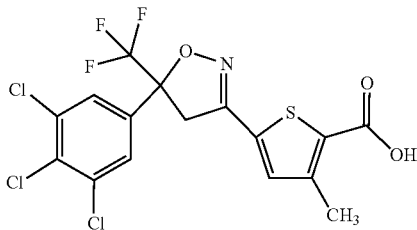 [SMILES: Cc1cc(C2=NOC(c3cc(Cl)c(Cl)c(Cl)c3)(C(F)(F)F)C2)sc1C(=O)O]

by crystallization of a diastereomeric salt followed by repeated cycles of racemization followed by further resolution by diastereomeric salt formation. The method of resolution and cycles of racemization and resolution are labor intensive and costly. Direct formation of the desired (S)-enantiomer is advantageous. Direct formation of enantiomers of certain 5-aryl-5-trifluoromethyl-4,5-dihydro-isoxazoles are known in the art, including those described in US2014/0206633, US 2014/0350261, WO 2013/116236, WO 2014/081800, Angew, Chem. Int. Ed. 2010, 49, 5762-5766, and WO 2017/176948.

SUMMARY

The present invention provides a method of making isoxazoline compounds, in particular lotilaner, using a cinchona alkaloid directed asymmetric hydroxylamine/enone cascade reaction that avoids costly and labor intensive cycles of resolution and racemization and further resolution.

In one aspect the present invention relates to a process for the preparation of an enantiomerically pure isoxazoline compound of formula (1)

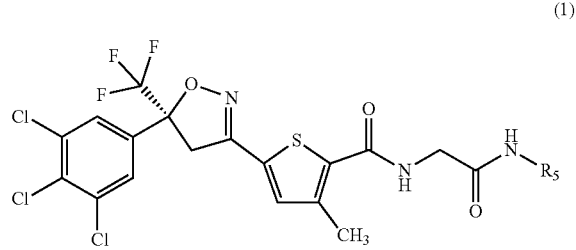

(1)

wherein $R_5$ is a $C_1$-$C_4$ aliphatic chain which optionally contains a double or triple bond, wherein the chain is optionally substituted with 1 to 5 substituents independently selected from the group consisting of halogen, cyano, nitro, hydroxyl, oxo, $C_3$-$C_6$ cycloalkyl, $C_1$-$C_4$ alkoxy, $C_1$-$C_7$ aminocarbonyl, —N($C_1$-$C_4$ alkyl)$_2$, —S$C_1$-$C_4$ alkyl, —S(O)$C_1$-$C_4$ alkyl, and —SO$_2$$C_1$-$C_4$ alkyl, comprising the steps of (i) reacting a compound of formula (2) with hydroxylamine

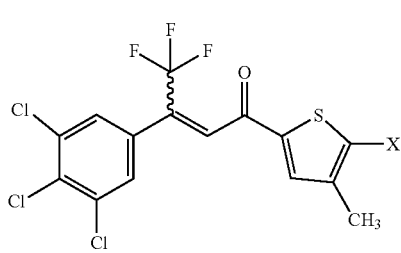

(2)

wherein X is selected from the group consisting of halogen and —C(O)O$R_4$ wherein $R_4$ is a $C_1$-$C_4$ alkyl and an appropriate base and a compound of formula (3)

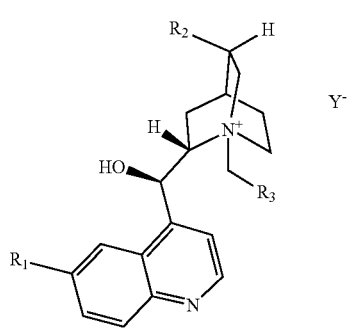

(3)

wherein Y$^-$ is an anion,
$R_1$ is selected from the group consisting of hydrogen and methoxy,
$R_2$ is selected from the group consisting of ethyl and vinyl,
$R_3$ is selected from the group consisting of aryl optionally substituted with 1 to 5 substituents independently selected from the group consisting of nitro, halogen, amino, trifluoromethyl, $C_1$-$C_4$ alkyl, $C_1$-$C_4$ alkoxy, and benzyloxy, and heteroaryl optionally substituted with 1 to 3 substituents independently selected from the group consisting of halogen, trifluoromethyl, $C_1$-$C_4$ alkyl, and $C_1$-$C_4$ alkoxy,
to give a compound of formula (4)

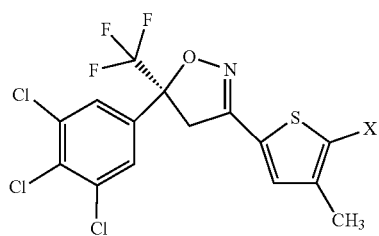

(4)

(ii) converting X of a compound of formula (4) to a carboxylic acid to give the compound of formula (5)

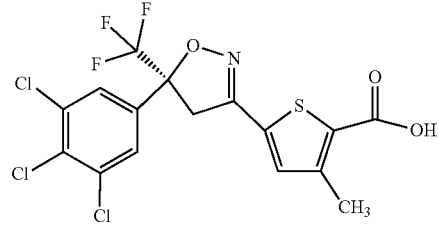

(5)

(iii) optionally crystallizing the compound of formula (5) with a solvent selected from the group consisting of $C_{1-5}$ alcohol, $C_{2-5}$ alkyl cyanide, $C_{3-9}$ alkyl ketone, $C_{2-8}$ alkyl ether, and $C_{2-8}$ alkyl acetate, and optionally with an anti-solvent selected from the group consisting of water and $C_{5-8}$ hydrocarbon, and (iv) coupling the compound of formula 5 with an appropriate amine.

In another aspect the present invention relates to a process for the preparation of enantiomerically pure lotilaner of formula (1a)

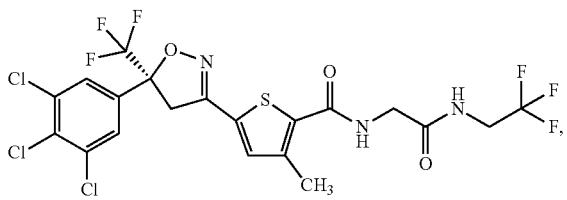

(1a)

comprising the steps of (i) reacting a compound of formula (2) with hydroxylamine

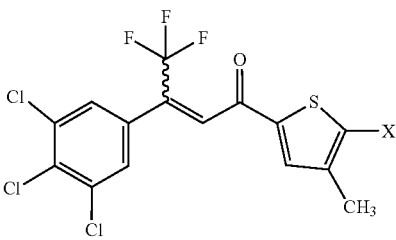

(2)

wherein X is selected from the group consisting of halogen and —C(O)OR$_4$ wherein R$_4$ is a C$_1$-C$_4$ alkyl and an appropriate base and a compound of formula (3)

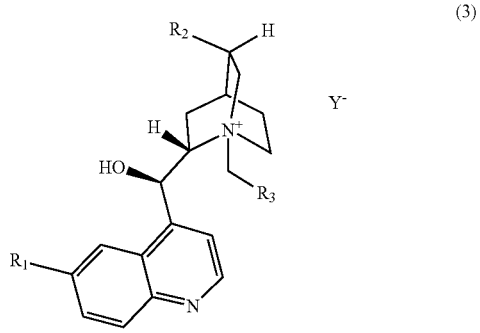

(3)

wherein Y$^-$ is an anion,
R$_1$ is selected from the group consisting of hydrogen and methoxy,
R$_2$ is selected from the group consisting of ethyl and vinyl,
R$_3$ is selected from the group consisting of aryl optionally substituted with 1 to 5 substituents independently selected from the group consisting of nitro, halogen, amino, trifluoromethyl, C$_1$-C$_4$ alkyl, C$_1$-C$_4$ alkoxy, and benzyloxy, and heteroaryl optionally substituted with 1 to 3 substituents independently selected from the group consisting of halogen, trifluoromethyl, C$_1$-C$_4$ alkyl, and C$_1$-C$_4$ alkoxy,
to give a compound of formula (4)

(4)

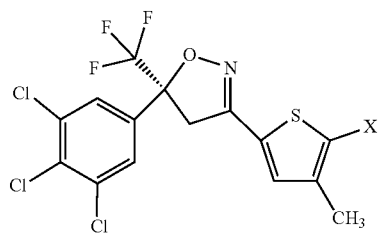

(ii) converting X of a compound of formula (4) to a carboxylic acid to give the compound of formula (5)

(5)

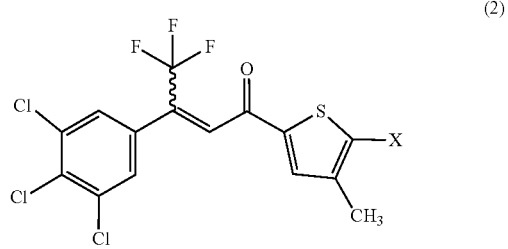

(iii) optionally crystallizing the compound of formula (5) with a solvent selected from the group consisting of C$_{1-5}$ alcohol, C$_{2-5}$ alkyl cyanide, C$_{3-9}$ alkyl ketone, C$_{2-8}$ alkyl ether, and C$_{2-8}$ alkyl acetate, and optionally with an anti-solvent selected from the group consisting of water and C$_{5-8}$ hydrocarbon, and
(iv) coupling the compound of formula 5 with either 2-amino-2',2',2'-trifluoroethyl-acetamide or the sequential reaction of glycine optionally carboxyl protected, followed by deprotection if required and coupling with 2,2,2-trifluorethylamine.

In one aspect the present invention provides a process for the preparation of an enantiomerically pure isoxazoline compound of formula (1), wherein R$_5$ is a C$_1$-C$_4$ aliphatic chain which optionally contains a double or triple bond, wherein the chain is optionally substituted with 1 to 5 substituents independently selected from the group consisting of halogen, cyano, nitro, hydroxyl, oxo, C$_3$-C$_6$ cycloalkyl, C$_1$-C$_4$ alkoxy, C$_1$-C$_7$ aminocarbonyl, —N(C$_1$-C$_4$ alkyl)$_2$, —SC$_1$-C$_4$ alkyl, —S(O)C$_1$-C$_4$ alkyl, and —SO$_2$C$_1$-C$_4$ alkyl, characterized by the preparation of enantiomerically pure compound of formula (4)

(4)

wherein X is selected from the group consisting of halogen and —C(O)OR$_4$ wherein R$_4$ is C$_1$-C$_4$ alkyl, comprising the steps of
(i) reacting a compound of formula (2) with hydroxylamine (2)

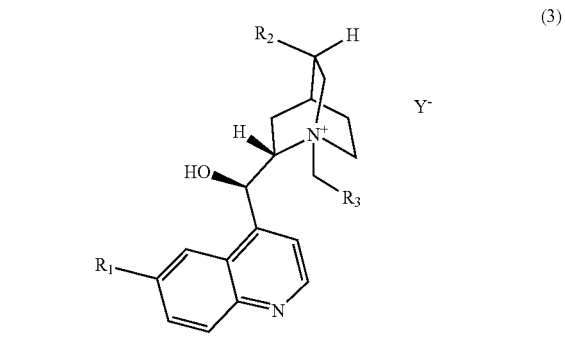

wherein X is selected from the group consisting of halogen and —C(O)OR$_4$ wherein R$_4$ is a C$_1$-C$_4$ alkyl and an appropriate base and a compound of formula (3)

(3)

wherein Y⁻ is an anion
R₁ is selected from the group consisting of hydrogen and methoxy,
R₂ is selected from the group consisting of ethyl and vinyl,
R₃ is selected from the group consisting of aryl optionally substituted with 1 to 5 substituents independently selected from the group consisting of nitro, halogen, amino, trifluoromethyl, $C_1$-$C_4$ alkyl, $C_1$-$C_4$ alkoxy, and benzyloxy, and heteroaryl optionally substituted with 1 to 3 substituents independently selected from the group consisting of halogen, trifluoromethyl, $C_1$-$C_4$ alkyl, and $C_1$-$C_4$ alkoxy.

DETAILED DESCRIPTION OF A PREFERRED EMBODIMENT

The invention is further illustrated by Scheme 1. In Scheme 1 all products can be isolated and purified by techniques well known in the art, such as extraction, evaporation, trituration, chromatography, and recrystallization.

invention encompasses the use of the E-isomer, the Z-isomer and mixtures thereof in any ratio. Particularly preferred compounds of formula (2) are those wherein X is chloro or bromo, even more preferred is bromo. Other particularly preferred compounds of formula (2) are those wherein X is —C(O)OR₄ and R₄ is selected from the group of methyl and ethyl, even more preferred methyl. Particularly preferred compounds of formula (3) are those wherein R₁ is methoxy.

A compound of formula (3) is typically, by reference to the compound of formula (2), used in a molar ratio of 0.001 to 10, more typically 0.01 to 1, even more typically 0.05 to 0.5.

Examples of appropriate bases include lithium hydroxide, sodium hydroxide, potassium hydroxide, barium hydroxide, cesium hydroxide, sodium phosphate, potassium phosphate, sodium methoxide, potassium hydroxide, potassium t-butoxide, and the like. In an embodiment, an appropriate base is selected from the group consisting of lithium hydroxide, sodium hydroxide, potassium hydroxide, barium hydroxide, cesium hydroxide, sodium phosphate, potassium phosphate,

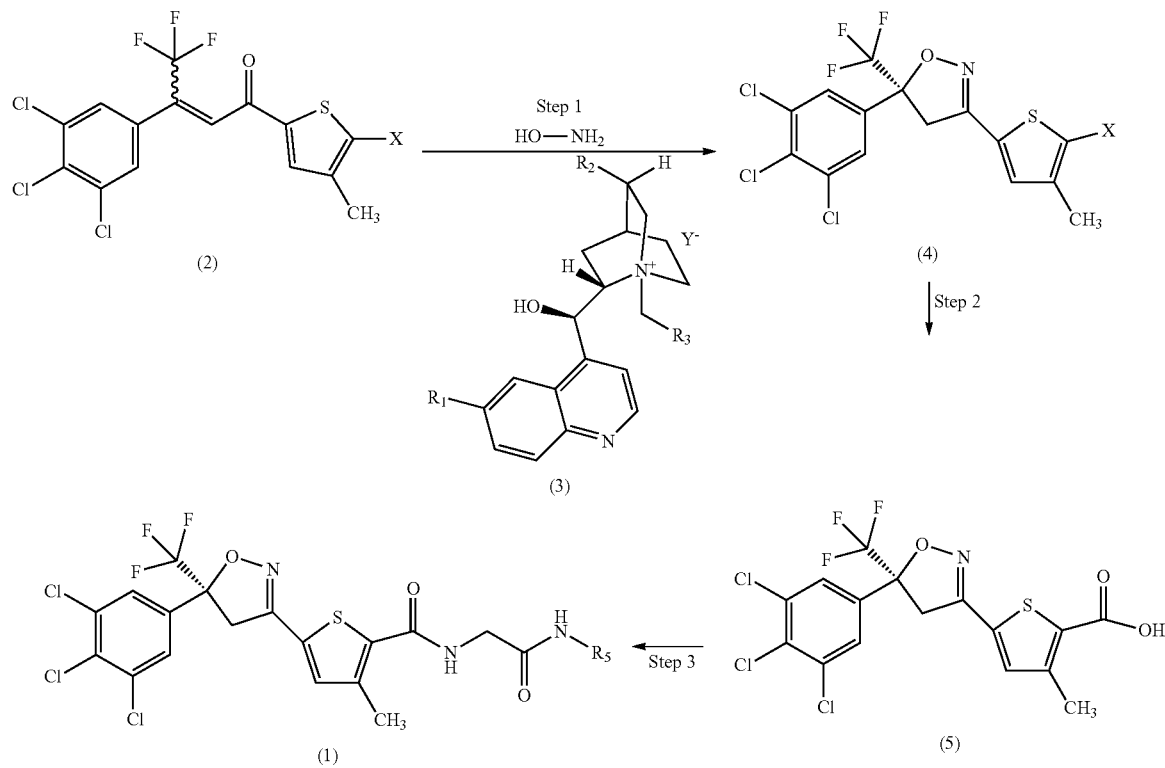

Scheme 1

Scheme 1, step 1, depicts a cinchona alkaloid directed asymmetric hydroxylamine/enone cascade reaction using a compound of formula (2) wherein X is selected from the group consisting of halogen and —C(O)OR₄ wherein R₄ is a $C_1$-$C_4$ alkyl with hydroxyl amine and an appropriate base in the presence of a compound of formula (3) to give an enantiomerically pure compound of formula (4).

The person of skill in the art will appreciate that a compound of formula (2) exists as geometric isomers. In the compound of formula (2) the bond from the double bond to the CF₃ group denotes such geometric isomers, including an E-isomer, a Z-isomer and mixtures thereof and the present sodium methoxide, potassium hydroxide, potassium t-butoxide, and mixtures thereof. Typically, by reference to the compound of formula (2), the base is used in a molar ratio of 1 to 10, more typically 1 to 5, even more typically 2 to 4. Of course, the skilled person will appreciate that additional base may be used if the hydroxylamine is used as a salt.

The reaction depicted in Scheme 1, step 1, is carried out in a solvent, such as a lower alcohol, such as methanol, ethanol, and isopropanol, a chlorinate solvent such as methylene chloride and chloroform, an ether solvent such as tetrahydrofuran, 2-methyltetrahydrofuran, diisopropyl ether and methyl-t-butyl ether, t-amyl methyl ether, ethyl-t-butyl ether, an aromatic solvent such as toluene, chlorobenzene, and benzotrifluoride, or an alkane solvent such as hexane, heptane, methylcyclohexane, and cyclohexane; and mixtures of such solvents. Water may be added to the reaction. The reaction is typically carried out at temperatures of from −50° C. to 50° C., more typically −40° C. to 0° C., more typically −40° C. to −10° C., and even more typically −30° C. to −20° C., and generally required from 1 to 48 hours.

Typical compounds of formula (3) include (R)-[(2S)-1-[(3,5-bis-trifluoromethylphenyl)methyl]-5-vinyl-quinuclidin-1-ium-2-yl]-(6-methoxy-4-quinolyl)methanol bromide, (R)-[(2S)-1-[(3,5-bis-trifluoromethylphenyl)methyl]-5-vinyl-quinuclidin-1-ium-2-yl]-(6-methoxy-4-quinolyl)methanol chloride, (R)-[(2S)-1-[(3,5-bis-trifluoromethylphenyl)methyl]-5-vinyl-quinuclidin-1-ium-2-yl]-(4-quinolyl)methanol bromide, (R)-[(2S)-1-[(2,3,5-trifluorophenyl)methyl]-5-vinyl-quinuclidin-1-ium-2-yl]-(6-methoxy-4-quinolyl)methanol bromide, (R)-[(2S)-1-[(3,5-di-t-butylphenyl)methyl]-5-vinyl-quinuclidin-1-ium-2-yl]-(6-methoxy-4-quinolyl)methanol bromide, and (R)-[(2S)-1-[(anthracen-9-yl)methyl]-5-vinyl-quinuclidin-1-ium-2-yl]-(6-methoxy-4-quinolyl)methanol bromide.

Scheme 1, step 2, depicts converting X of a compound of formula (4) to a carboxylic acid of the compound of formula (5). A compound of formula (4) in which X is halogen can be converted to the compound of formula (5) by metallating the X-position with a Grignard reagent or a halogen-metal exchange with an alkyllithium and reacting the metallated species with carbon dioxide or a reagent that can be elaborated to a carboxylic acid. Such reactions are readily carried out and are well known. See WO 2014/090918. A compound of formula (4) in which X is —C(O)OR$_4$ is readily converted to the compound of formula (5) by hydrolysis. Such reactions are readily carried out and are well known.

Scheme 1, step 3, depicts coupling the compound of formula (5) with an appropriate amine to give an isoxazoline compound of formula (1), such as lotilaner, which is a compound of formula (1a). According to step (iv) of the present reaction, depending on the appropriate amine used, the coupling step may give an isoxazoline compound other than lotilaner. An appropriate amine refers to a compound of formula (6),

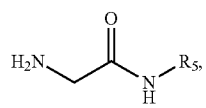

(6)

wherein R$_5$ is a C$_1$-C$_4$ aliphatic chain which optionally contains a double or triple bond, wherein the chain is optionally substituted with 1 to 5 substituents independently selected from the group consisting of halogen, cyano, nitro, hydroxyl, oxo, C$_3$-C$_6$ cycloalkyl, C$_1$-C$_4$ alkoxy, C$_1$-C$_7$ aminocarbonyl, —N(C$_1$-C$_4$ alkyl)$_2$, —SC$_1$-C$_4$ alkyl, —S(O)C$_1$-C$_4$ alkyl, and —SO$_2$C$_1$-C$_4$ alkyl. In an aspect, R$_5$ is C$_1$-C$_2$ alkyl optionally substituted with 1 to 3 substituents independently selected from the group consisting of halogen, cyano, nitro, hydroxyl, and oxo. In another aspect, R$_5$ is C$_1$-C$_2$ alkyl optionally substituted with 1 to 3 halogen substituents. In another aspect, R$_5$ is C$_1$-C$_2$ alkyl optionally substituted with 1 to 3 fluoro substituents. In another aspect, R$_5$ is ethyl optionally substituted with 1 to 3 halogen substituents. In another aspect, R$_5$ is ethyl optionally substituted with 1 to 3 fluoro substituents. In another aspect, R$_5$ is ethyl substituted with 1 to 3 fluoro substituents. In another aspect, R$_5$ is ethyl substituted with 3 fluoro substituents.

An exemplary appropriate amine is either 2-amino-2',2',2'-trifluoroethyl-acetamide, which is a compound of formula (7),

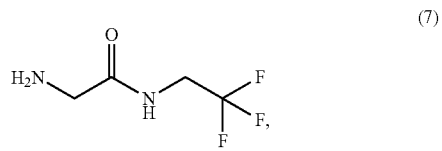

(7)

or the sequential reaction of glycine optionally carboxyl protected, followed by coupling with 2,2,2-trifluorethylamine. Such coupling reactions of carboxylic acids or activated carboxylic acid derivatives such as acid halides with amines to form amides are well known in the art. The use of carboxyl protected glycine, deprotection, and an amide coupling with 2,2,2-trifluorethylamine is likewise readily accomplished. See WO 2010/070068 and WO 2014/090918.

In another aspect the present invention relates to a process for the preparation of an enantiomerically pure compound of formula (5)

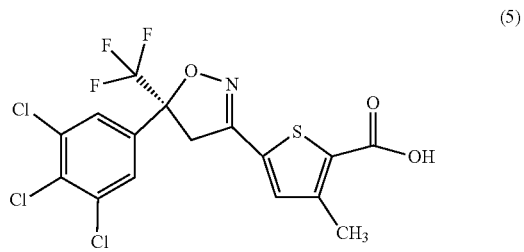 [SMILES: Cc1cc(C2=NO[C@@](c3cc(Cl)c(Cl)c(Cl)c3)(C(F)(F)F)C2)sc1C(=O)O]

(5)

comprising the steps of
(i) reacting a compound of formula (2) with hydroxylamine

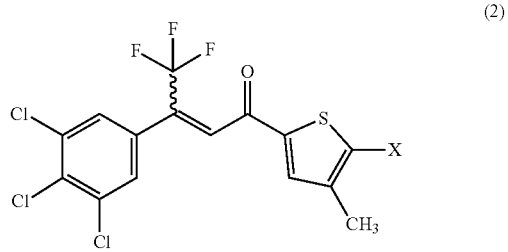

(2)

wherein X is selected from the group consisting of halogen and —C(O)OR$_4$ wherein R$_4$ is a C$_1$-C$_4$ alkyl and an appropriate base and a compound of formula (3)

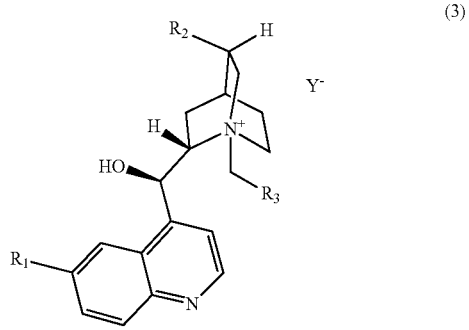

(3)

wherein Y$^-$ is an anion,
R$_1$ is selected from the group consisting of hydrogen and methoxy,
R$_2$ is selected from the group consisting of ethyl and vinyl,
R$_3$ is selected from the group consisting of aryl optionally substituted with 1 to 5 substituents independently selected from the group consisting of nitro, halogen, amino, trifluoromethyl, C$_1$-C$_4$ alkyl, C$_1$-C$_4$ alkoxy, and benzyloxy, and heteroaryl optionally substituted with 1 to 3 substituents independently selected from the group consisting of halogen, trifluoromethyl, C$_1$-C$_4$ alkyl, and C$_1$-C$_4$ alkoxy,
to give a compound of formula (4)

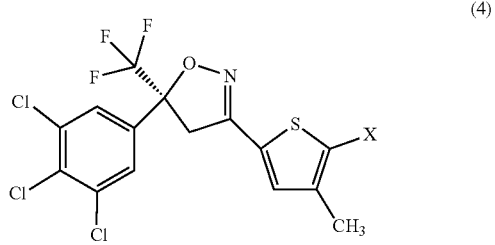

(4)

(ii) converting X of a compound of formula (4) to a carboxylic acid to give the compound of formula (5), and
(iii) optionally crystallizing the compound of formula (5) with a solvent selected from the group consisting of C$_{1-5}$ alcohol, C$_{2-5}$ alkyl cyanide, C$_{3-9}$ alkyl ketone, C$_{2-8}$ alkyl ether, and C$_{2-8}$ alkyl acetate, and optionally with an anti-solvent selected from the group consisting of water and C$_{5-8}$ hydrocarbon.

In another aspect, the (iii) crystallizing step in the process for the preparation of an enantiomerically pure compound of formula (5) occurs. In another aspect, the anti-solvent in (iii) is present.

The present disclosure also provides a process for improving the enantiomeric purity of a compound of formula (5), 3-methyl-5-[(5S)-5-(3,4,5-trichlorophenyl)-5-(trifluoromethyl)-4H-isoxazol-3-yl]thiophene-2-carboxylic acid, comprising: crystallization from a solvent(s) selected from the group consisting of C$_{1-5}$ alcohol, C$_{2-5}$ alkyl cyanide, C$_{3-9}$ alkyl ketone, C$_{2-8}$ alkyl ether, and C$_{2-8}$ alkyl acetate, and optionally with an anti-solvent selected from the group consisting of water and C$_{5-8}$ hydrocarbon.

The enantiomeric purity of a compound of 3-methyl-5-[(5S)-5-(3,4,5-trichlorophenyl)-5-(trifluoromethyl)-4H-isoxazol-3-yl]thiophene-2-carboxylic acid may be improved by crystallization under controlled conditions by crystallization from a solvent or a mixture of solvents. In practice it has been found that C$_{1-5}$ alcohol, C$_{2-5}$ alkyl cyanide, C$_{3-9}$ alkyl ketone, C$_{2-8}$ alkyl ether, C$_{2-8}$ alkyl acetate, and preferably C$_{1-5}$ alcohol, C$_{2-5}$ alkyl cyanide, and C$_{3-9}$ alkyl ketone are useful solvents for such purification.

Thus, the present disclosure provides a process for making enantiomerically pure isoxazoline compound of formula (1) characterized by improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a C$_{2-5}$ alkyl cyanide. In a preferred embodiment the C$_{2-5}$ alkyl cyanide is acetonitrile.

The present disclosure provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid (the compound of formula (5)) comprising: crystallization from a C$_{1-5}$ alcohol. In a preferred embodiment the C$_{1-5}$ alcohol is isopropanol.

The present invention provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a C$_{3-9}$ alkyl ketone. In a preferred embodiment the C$_{3-9}$ alkyl ketone is acetone.

As used herein, the term "enantiomerically pure" refers to the (S)-enantiomer that is present in greater than 90% (i.e., 80% or greater enantiomeric excess, or e.e.). In one embodiment, the term "enantiomerically pure" refers to the (S)-enantiomer that is present in greater than 92% (i.e., 84% or greater e.e.). In one embodiment, the term "enantiomerically pure" refers to the (S)-enantiomer that is present in greater than 94% (i.e., 88% or greater e.e.). In one embodiment, the term "enantiomerically pure" refers to the (S)-enantiomer that is present in greater than 95% (i.e., 90% or greater e.e.). In one embodiment, the term "enantiomerically pure" refers to the (S)-enantiomer that is present in greater than 96% (i.e., 92% or greater e.e.). In one embodiment, the term "enantiomerically pure" refers to the (S)-enantiomer that is present in greater than 97% (i.e., 94% or greater e.e.). In one embodiment, the term "enantiomerically pure" refers to the (S)-enantiomer that is present in greater than 98% (i.e., 96% or greater e.e.). In one embodiment, the term "enantiomerically pure" refers to the (S)-enantiomer that is present in greater than 99% (i.e., 98% or greater e.e.). In one embodiment, the term "enantiomerically pure" refers to the (S)-enantiomer that is present in greater than 99.8% (i.e., 99.6% or greater e.e.).

The use of an anti-solvent may be advantageous. As used in this context an "anti-solvent" refers to a solvent in which a compound of formula (5) is significantly less soluble relative to the selected solvent(s). Preferably, when an anti-solvent is used it is miscible with the selected solvent.

Also provided is a process for improving the enantiomeric purity of a compound of formula (5), above, comprising: crystallization from a solvent(s) selected from the group consisting of C$_{1-5}$ alcohol, C$_{2-5}$ alkyl cyanide, C$_{3-9}$ alkyl ketone, C$_{2-8}$ alkyl ether, and C$_{2-8}$ alkyl acetate, further comprising an anti-solvent.

The present invention provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid (the compound of formula (5)) comprising: crystallization from a $C_{1-5}$ alcohol/water. In a preferred embodiment the ratio of $C_{1-5}$ alcohol to water is about 9:1 (v/v). In a preferred embodiment the $C_{1-5}$ alcohol is isopropanol. In an even more preferred embodiment the $C_{1-5}$ alcohol is isopropanol and ratio of isopropanol to water is 9:1 (v/v).

Thus, the present invention provides a process for making enantiomerically pure isoxazoline compound of formula (1) characterized by improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a $C_{1-5}$ alcohol/water. In a preferred embodiment the ratio of $C_{1-5}$ alcohol to water is about 9:1 (v/v). In a preferred embodiment the $C_{1-5}$ alcohol is isopropanol. In an even more preferred embodiment the $C_{1-5}$ alcohol is isopropanol and ratio of isopropanol to water is 9:1 (v/v).

The present invention provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a $C_{3-9}$ alkyl ketone/water. In a preferred embodiment the ratio of $C_{3-9}$ alkyl ketone to water is about 9:1 (v/v). In a preferred embodiment the $C_{3-9}$ alkyl ketone is acetone. In an even more preferred embodiment the $C_{3-9}$ alkyl ketone is acetone and ratio of acetone to water is 9:1 (v/v).

Thus, the present invention provides a process for making enantiomerically pure isoxazoline compound of formula (1) characterized by improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a $C_{3-9}$ alkyl ketone/water. In a preferred embodiment the ratio of $C_{3-9}$ alkyl ketone to water is about 9:1 (v/v). In a preferred embodiment the $C_{3-9}$ alkyl ketone is acetone. In an even more preferred embodiment the $C_{3-9}$ alkyl ketone is acetone and ratio of acetone to water is 9:1 (v/v).

Preferred anti-solvents are $C_{5-8}$ hydrocarbon and water. In particular, preferred anti-solvents are selected from the group consisting of water, pentane, hexane, heptane, cyclohexane, and methylcyclohexane. A particularly preferred anti-solvent is methylcyclohexane. The ratio of selected solvent and anti-solvent is not critical and typically ranges from 2:1 to 1:6 (v/v).

Thus, the present invention provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a C1-5 alcohol and a C5-8 hydrocarbon. In a preferred embodiment the C1-5 alcohol is selected from the group consisting of ethanol and isopropanol.

The present invention provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a $C_{2-8}$ alkyl ether and a $C_{5-8}$ hydrocarbon. In a preferred embodiment the $C_{2-8}$ alkyl ether is selected from the group consisting of tetrahydrofuran and 2-methyltetrahydrofuran.

The present invention provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a $C_{2-8}$ alkyl acetate and a $C_{5-8}$ hydrocarbon. In a preferred embodiment the $C_{2-8}$ alkyl acetate is selected from the group consisting of ethyl acetate and isopropyl acetate.

The present invention provides a process for improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a $C_{3-9}$ alkyl ketone and a $C_{5-8}$ hydrocarbon. In a preferred embodiment the $C_{3-9}$ alkyl ketone is selected from the group consisting of acetone and methyl ethyl ketone.

As used herein, the term "halogen" refers to fluorine, chlorine, bromine, and iodine atoms. In particular, the term "halogen" refers to fluorine, chlorine, and bromine atoms. Even more particularly, the term "halogen" refers to chlorine and bromine atoms.

The term "anion" as it relates to $Y^-$ refers to a negatively charged organic or inorganic group. For example, $Y^-$ can be tosylate, brosylate, mesylate, nosylate, triflate, acetate, and the like or can be halide, sulfate, phosphate, hydroxide, boron tetrafluoride, and the like. In one embodiment, Y is a halide. In one embodiment Y is chloride or bromide.

The term "aryl" refers to phenyl, naphthyl, anthracenyl, and the like. In one embodiment "aryl" is phenyl. In one embodiment "aryl" is anthracen-9-yl.

The term "heteroaryl" refers to fully unsaturated ring containing at least one heteroatom selected from the group consisting of nitrogen, oxygen, and sulfur, including pyridyl, pyrimidyl, pyrazinyl, indoly, quinolinyl, acridinyl, and the like.

The term "$C_1$-$C_4$ alkyl" refers to straight or branched chain alkyl groups with one to four carbon atoms.

The term "$C_1$-$C_4$ alkoxy" refers to a $C_1$-$C_4$ alkyl group attached through an oxygen atom.

The term "about" when used in connection with a measurable numerical variable, refers to the indicated value of the variable and to all values of the variable that are within the experimental error of the indicated value or within +10 percent of the indicated value, whichever is greater.

The term "$C_1$-$C_4$ aliphatic chain which may optionally contain double or triple bonds" refers to straight, branched, or non-aromatic cyclic alkyl group having from one to four carbon atoms and optionally containing a double or triple bond, for example, methyl, ethyl, ethynyl, propyl, propenyl, butynyl, and the like.

The term "$C_{1-5}$ alcohol" refers to a straight or branched alkanol having from one to five carbon atoms, for example methanol, ethanol, n-propanol, iso-propanol, 1-butanol, 1,3-propanediol, and the like.

The term "$C_{2-5}$ alkyl cyanide" refers to straight or branched alkyl cyanides having a total of two to five carbon atoms, for example acetonitrile, proprionitrile, and butyronitrile.

The term "$C_{3-9}$ alkyl ketone" refers to a straight, branched, or cyclic alkyl group having an oxo group and having a total of from three to nine carbon atoms, for example acetone, methyl ethyl ketone, and cyclohexanone.

The term "$C_{2-8}$ alkyl ether" refers to a straight, branched, or cyclic alkyl ether having a total of from two to eight carbon atoms, for example diethyl ether, methyl t-butyl ether, t-amyl methyl ether, ethyl-t-butyl ether, tetrahydrofuran (THF), 2-methyl THF, dioxane, and the like.

The term "$C_{3-8}$ alkyl acetate" refers to straight or branched alkyl esters of acetic acid having a total of three to eight carbons, for example, methyl acetate, ethyl acetate, isopropyl acetate, butyl acetate, isobutyl acetate, and the like.

The term "$C_{5-8}$ hydrocarbon" refers to a straight, branched, or cyclic saturated alkyl hydrocarbon, for example, pentane, hexane, heptane, octane, cyclopentane, cyclohexane, methyl cyclohexane and the like.

It is understood that the terms "crystallize," "crystallizing," and "crystallization" refer to complete dissolution followed by precipitation and slurry processes that do not involve complete dissolution. Slurry processes include those that encompass continuation of stirring following precipitation after complete dissolution.

The invention is still further illustrated by the following examples. The examples are intended to be illustrative only and not intended to limit the invention in any way.

Example 1

(5S)-3-(5-Bromo-4-methyl-2-thienyl)-5-(3,4,5-trichlorophenyl)-5-(trifluoromethyl)-4H-isoxazole

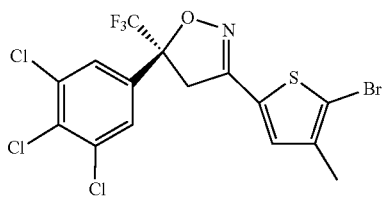 [SMILES: Cc1cc(C2=NO[C@@](c3cc(Cl)c(Cl)c(Cl)c3)(C(F)(F)F)C2)sc1Br]

Combined (Z/E)-1-(5-bromo-4-methyl-2-thienyl)-4,4,4-trifluoro-3-(3,4,5-trichlorophenyl)but-2-en-1-one (1.0 g, 2.1 mmol) and (R)-[(2S)-1-[[3,5-bis(trifluoromethyl)phenyl]methyl]-5-vinyl-quinuclidin-1-ium-2-yl]-(6-methoxy-4-quinolyl)methanol bromide (135 mg, 0.2138 mmol, 0.1 eq.) in dichloromethane (100 mL) under nitrogen. The solution was cooled in the range −15° C. to −10° C. and slowly added a solution of hydroxylamine in water (386 µL, 6.25 mmol, 16.2 mol/L, 3.0 eq.) and sodium hydroxide (0.70 mL, 7.0 mmol, 10 M, 3.3 eq.) to the reaction mixture maintaining an internal temperature of −10° C. After stirring at −10° C. for 7 hours, the chiller was turned off and the reaction was left stirring overnight at room temperature. The reaction mixture was transferred to a round bottom flask and concentrated under reduced pressure at room temperature to give a solid. The solid was dissolved in ethyl acetate (3 mL) and purified by automated flash chromatography on silica gel by eluting with EtOAc:Hexane (1:1). The solvent was removed from the product containing fractions under reduced pressure at 40° C. to give as a light yellow solid (0.833 g, 81%).

Example 2

(5S)-3-(5-Bromo-4-methyl-2-thienyl)-5-(3,4,5-trichlorophenyl)-5-(trifluoromethyl)-4H-isoxazole

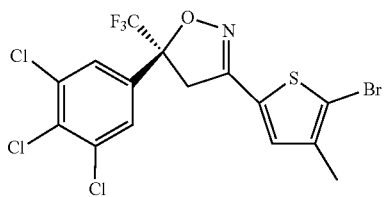 [SMILES: Cc1cc(C2=NO[C@@](c3cc(Cl)c(Cl)c(Cl)c3)(C(F)(F)F)C2)sc1Br]

Combined (Z/E) 1-(5-bromo-4-methyl-2-thienyl)-4,4,4-trifluoro-3-(3,4,5-trichlorophenyl)but-2-en-1-one (10.0 g, 20.9 mmol) and (R)-[(2S)-1-[[3,5-bis(trifluoromethyl)phenyl]methyl]-5-vinyl-quinuclidin-1-ium-2-yl]-(6-methoxy-4-quinolyl)methanol bromide (2.14 mmol, 0.1 eq.) in dichloromethane (250 mL) under nitrogen. The solution was cooled to the range of −10° C. to −15° C. and then slowly added a solution of hydroxylamine in water (3.9 mL, 63.2 mmol, 16.2 mol/L, 3.0 eq.) and sodium hydroxide (7.0 mL, 70 mmol, 10 M, 3.3 eq.) maintaining an internal temperature in the range of −10° C. to −15° C. After stirring 18 hours at −15° C. to −10° C. the reaction mixture was then transferred to a round bottom flask and concentrated under reduced pressure at room temperature to give a solid. The solid was then dissolved in ethanol (90 mL) at 50° C., stirred for 30 minutes at 50° C. (water bath), and then water (300 mL) was added slowly dropwise while stirring to give a suspension. The suspension was filtered and the above evaporation and recrystallization were repeated three times. The solid was dried in a vacuum oven at 25-30° C. for four days to provide 10.34 g (97.4%). The combined solids were evaluated by chiral HPLC which indicated 91.34% S-isomer and 8.67% R-isomer.

Example 3a (5S)-3-(5-Bromo-4-methyl-2-thienyl)-5-(3,4,5-trichlorophenyl)-5-(trifluoromethyl)-4H-isoxazole

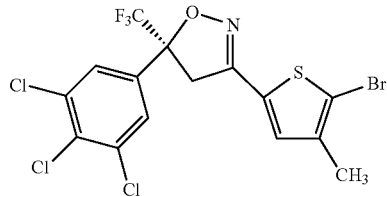 [SMILES: Cc1cc(C2=NO[C@@](c3cc(Cl)c(Cl)c(Cl)c3)(C(F)(F)F)C2)sc1Br]

Combined (Z/E) 1-(5-bromo-4-methyl-2-thienyl)-4,4,4-trifluoro-3-(3,4,5-trichlorophenyl)but-2-en-1-one (50.0 g, 104.5 mmol) and (R)-[(2S)-1-[[3,5-bis(tert-butyl)phenyl]methyl]-5-vinyl-quinuclidin-1-ium-2-yl]-(6-methoxy-4-quinolyl)methanol bromide (0.11 eq.) in dichloromethane (100 mL) and ethyl t-butyl ether (400 mL). The reaction mixture was stirred at 30° C. for 30 minutes and then cooled to the range of −20° C. then slowly added a solution of hydroxylamine in water (50%, 40 mL, 313 mmol, 3.0 eq.) and sodium hydroxide (34.5 mL, 345 mmol, 10 M, 3.3 eq.) maintaining an internal temperature in the range of −15° C. to −20° C. After stirring 18 hours at −15° C. to −20° C. aqueous hydrochloric acid (1N, 500 mL) was added and the reaction mixture was stirred at 15° C. to 20° C. then the stirring was stopped and after 30 minutes the phases were separated. The organic layer was extracted with aqueous hydrochloric acid (1N, 75 mL), the layers separated and the organic layer again extracted with aqueous hydrochloric acid (1N, 100 mL). The organic layer was separated and extracted with saturated aqueous sodium bicarbonate (75 mL) and the layers were separated and again the organic layer was extracted with saturated aqueous sodium bicarbonate (100 mL). The layers were separated and the organic layer was dried over sodium sulfate (10 g). The organic layer was filtered, the cake washed with ethyl t-butyl ether (50 mL) and then montmorillonite clay (50 g) was added and the mixture was stirred at 10° C. to 20° C. After 2 hours the reaction mixture was filtered, the cake rinsed with ethyl t-butyl ether (50 mL) and the filtrate was concentrated to about 100 ml, twice added THF and concentrated again to about 100 mL, and then added THF (150 mL) to obtain the title compound as a solution in THF. The solution was evaluated by chiral HPLC which indicated 96.5% S-isomer and 3.5% R-isomer.

Example 3b

3-Methyl-5-[(5S)-5-(3,4,5-trichlorophenyl)-5-(trifluoromethyl)-4H-isoxazol-3-yl]thiophene-2-carboxylic acid

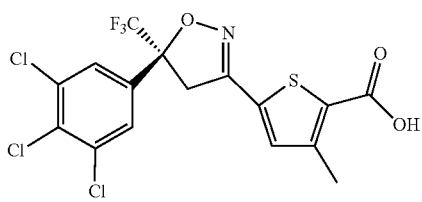 [SMILES: Cc1cc(C2=NO[C@@](c3cc(Cl)c(Cl)c(Cl)c3)(C(F)(F)F)C2)sc1C(=O)O]

A 22% solution of (5S)-3-(5-bromo-4-methyl-2-thienyl)-5-(3,4,5-trichlorophenyl)-5-(trifluoromethyl)-4H-isoxazole (185.0 g, 374.8 mmol) in THF was cooled to 0° C. to 5° C. A solution of ethyl magnesium chloride in THF (2 M, 300 mL, 1.6 eq) was added dropwise maintaining an internal temperature below 10° C. The reaction mixture was stirred at 15° C. to 20° C. for 2 to 4 hours. Then carbon dioxide gas (58 g, 3.5 eq) was introduced subsurface at 0° C. to 5° C. after passing through concentrated sulfuric acid (50 mL). The reaction mixture was stirred at 0° C. to 5° C. for 2 hours and an 8% aqueous sodium chloride solution (601 g) was added dropwise at below 10° C., followed by addition of 37% aqueous HCl solution (92.5 g) at below 0° C. to give the title compound.

Example 3c

3-Methyl-N-[2-oxo-2-(2,2,2-trifluoroethylamino)ethyl]-5-[(5S)-5-(3,4,5-trichlorophenyl)-5-(trifluoromethyl)-4H-isoxazol-3-yl]thiophene-2-carboxamide

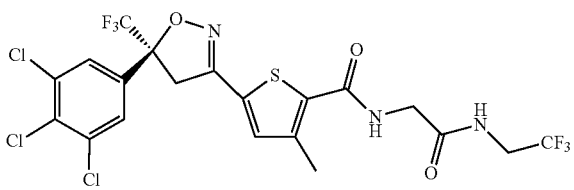 [SMILES: Cc1cc(C2=NO[C@@](c3cc(Cl)c(Cl)c(Cl)c3)(C(F)(F)F)C2)sc1C(=O)NCC(=O)NCC(F)(F)F]

A solution of 3-methyl-5-[(5S)-5-(3,4,5-trichlorophenyl)-5-(trifluoromethyl)-4H-isoxazol-3-yl]thiophene-2-carboxylic acid (101.5 g, 221.3 mmol) in dichloromethane (DCM) (1000 mL) was heated to 40° C. Thionyl chloride (50 g, 1.9 eq) was added dropwise and the reaction mixture was stirred at reflux for 2 to 4 hours. The reaction mixture was concentrated to 100 to 200 ml and DCM (500 mL) was added. Two more cycles of concentration followed by DCM addition were performed. In a separate vessel, a suspension of 2-amino-trifluoroethyl-acetamide HCl (50.26 g, 1.2 eq) in DCM (500 mL) was cooled to 0° C. to 5° C., triethylamine (70.15 g, 3.1 eq) was added, and the reaction mixture was stirred at 0° C. to 5° C. for 30 minutes. The acid chloride solution in DCM was then transferred to the reaction mixture containing 2-amino-trifluoroethyl-acetamide maintaining the internal temperature below 5° C. The reaction mixture was stirred at 0° C. to 5° C. for 2 to 4 hours. 1 N HCl (500 mL) was added dropwise and the reaction mixture was stirred at 15 to 25° C. for 30 minutes. The stirring was stopped and after 30 minutes the phases were separated. The organic layer was extracted with saturated sodium bicarbonate solution (1N, 1000 mL), the layers separated and the organic layer extracted with water (1000 mL). The layers were separated and the organic layer was concentrated under vacuum to 200 to 300 mL. Twice ethyl acetate (500 mL) was added and the batch was concentrated to 200 mL. The reaction mixture was heated to 55° C. and n-heptane (700 mL) was added dropwise at 55° C. After 1 hour, n-Heptane (1000 mL) was added dropwise and the mixture was stirred at 55° C. for three hours. The batch was gradually cooled to 35° C. over three hours, then to 20° C. over three hours. The batch was filtered and the cake was washed with n-heptane (200 mL). 113 g of the title compound was obtained after drying at 50° C. under vacuum for 12 hours.

Example 4a (5S)-3-(5-Bromo-4-methyl-2-thienyl)-5-(3,4,5-trichlorophenyl)-5-(trifluoromethyl)-4H-isoxazole

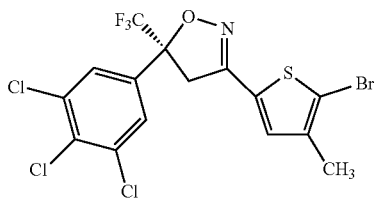 [SMILES: Cc1cc(C2=NO[C@@](c3cc(Cl)c(Cl)c(Cl)c3)(C(F)(F)F)C2)sc1Br]

To a mixture of butenone bromothiophene (658 g), (R)-[(2S)-1-[(3,5-di-t-butylphenyl)methyl]-5-vinyl-quinuclidin-1-ium-2-yl]-(6-methoxy-4-quinolyl)methanol bromide (57 g), dichloromethane (1120 g) and methyl tert-butyl ether (MTBE) (2586 g), cooled to approx. −30° C., was added a solution of hydroxylamine hydrochloride (261 g) in water (333 g, precooled to 0° C.) at −30° C., followed by addition of aqueous sodium hydroxide solution (32%, 548 g), also at −30° C. The reaction mixture was agitated at −30° C. for several hours until conversion is complete. The reaction mixture was warmed to 0-5° C. and transferred into a quench solution consisting of hydrochloric acid (37%, 286 g), ethanol (468 g) and water (600 g). The mixture was warmed to 40° C., the pH was checked to be pH=5-6 and the phases were separated. The organic layer was concentrated under reduced pressure and the distillate was replaced with fresh methyl tert-butyl ether (2 cycles, 1777 g each). Subsequently, the mixture was briefly heated to reflux and then cooled to −10° C. to trigger precipitation of the catalyst. The resulting suspension was filtered and optionally extracted by a solution of hydrochloric acid (37%, 240 g), sodium chloride (240 g) and water (1080 g), and optionally filtered by a filter bed of bleaching earth. The filtrate was washed with saturated bicarbonate solution (1200 g) and the organic layer was stored as an MTBE solution containing the product, (S)-isoxazolbromothiophene.

Example 4b

3-Methyl-5-[(5S)-5-(3,4,5-trichlorophenyl)-5-(trifluoromethyl)-4H-isoxazol-3-yl]thiophene-2-carboxylic acid

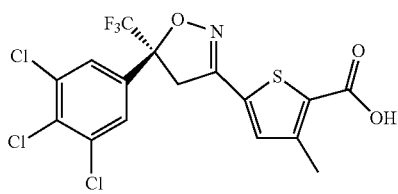 [SMILES: Cc1cc(C2=NO[C@@](c3cc(Cl)c(Cl)c(Cl)c3)(C(F)(F)F)C2)sc1C(=O)O]

The reaction mixture produced from Example 4a ((5S)-3-(5-Bromo-4-methyl-2-thienyl)-5-(3,4,5-trichlorophenyl)-5-(trifluoromethyl)-4H-isoxazole in MTBE) was charged to a reactor and concentrated. The distillate was replaced with fresh THF (2 cycles, 2136 g each). Ethylmagnesiumchloride (~25% in tetrahydrofuran, 933 g) was added after cooling to IT −10° C. After completion of the reaction (HPLC), gaseous carbon dioxide (236 g) was added as fast as possible below the surface at internal temperature −1° C. The reaction mixture was stirred at internal temperature 0° C. After completion of the reaction (HPLC), the reaction mixture was quenched by adding it slowly to a mixture containing sodium chloride (110 g), water (2235 g) and 37% hydrochloric acid (283 g) at ambient temperature. After mixing and settling, the phases were separated. The organic layer was concentrated and the distillate replaced by fresh acetonitrile (2 cycles, 1915 g each). The reaction mixture as briefly warmed to obtain a clear solution before it was cooled to −10° C. and the product was isolated by centrifugation and washed with pre-cooled acetonitrile (460 g). The wet (S)-Isoxazolthiophene carboxylic acid was dried at 50° C., ≤100 mbar in the vacuum dryer. The dry yield was 82% of theoretical yield. Purity: 100%, chiral purity, 99.8 a %.

Example 4c

3-Methyl-N-[2-oxo-2-(2,2,2-trifluoroethylamino)ethyl]-5-[(5S)-5-(3,4,5-trichlorophenyl)-5-(trifluoromethyl)-4H-isoxazol-3-yl]thiophene-2-carboxamide

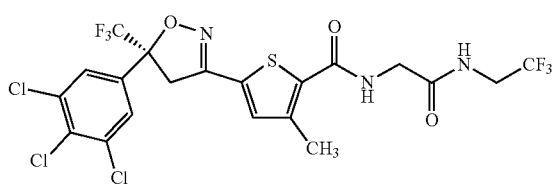 [SMILES: Cc1cc(C2=NO[C@@](c3cc(Cl)c(Cl)c(Cl)c3)(C(F)(F)F)C2)sc1C(=O)NCC(=O)NCC(F)(F)F]

S-Isoxazolthiophene carboxylic acid dry (from Example 4b, 20 g) and toluene (250 g) were charged to the reactor and the mixture is heated to 110° C. Thionyl chloride (14.0 g) was dosed slowly into the reaction mixture. After completion of the reaction toluene was distilled off at NMT 50° C. in vacuo and the residue was diluted with fresh dichloromethane (165 g).

In a separate reactor, 2-amino-trifluoroethyl-acetamide HCl (8.8 g) was suspended in dichloromethane (200 g) and triethylamine (13.7 g) was added at ambient temperature. The resulting mixture was cooled to 0° C. and the acyl chloride reaction mixture in dichloromethane was added at 0° C. over the course of 45 min. The combined reaction mixture was stirred for additional 1-8 hours at 0° C. and conversion was checked by IPC.

Upon sufficient conversion (IPC), the mixture was extracted with 1M hydrochloric acid (a mixture of 37% HCl (9.6 g) and water (77.4 g)) followed by saturated sodium hydrogen carbonate solution (8.4 g sodium hydrogen carbonate in 96.1 g water) and finally water (105 g).

The organic layer was concentrated at 40° C. in vacuo (≤300 mbar) and ethyl acetate (46.9 g) was added. The reaction mixture was heated to 55° C. and heptane (93.2 g) was added slowly. The mixture was seeded with 1.0 w/w % Lotilaner (0.26 g) and the turbid reaction mixture was stirred for 2 hours. More heptane (142.5 g) was added slowly and the resulting white suspension was stirred for 4 h. The thick suspension was slowly cooled to 35° C. within 6 h and then to 20° C. within 1 h. After 2 hours stirring, the product was isolated by centrifugation and washed with a mixture of ethyl acetate (8.5 g) and heptane (41.4 g). The product was dried at 50° C. and not more than 300 mbar. The dried yield was 87.6% of theoretical yield. Purity: 99.9a %, ROD: 99.78%.

Example 5

3-Methyl-5-[(5S)-5-(3,4,5-trichlorophenyl)-5-(trifluoromethyl)-4H-isoxazol-3-yl]thiophene-2-carboxylic acid

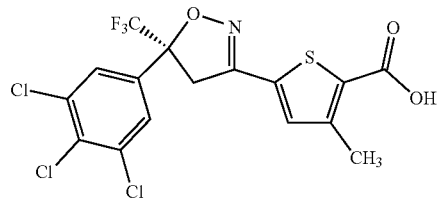 [SMILES: Cc1cc(C2=NO[C@@](c3cc(Cl)c(Cl)c(Cl)c3)(C(F)(F)F)C2)sc1C(=O)O]

A 22% solution of (5S)-3-(5-bromo-4-methyl-2-thienyl)-5-(3,4,5-trichlorophenyl)-5-(trifluoromethyl)-4H-isoxazole (185.0 g, 374.8 mmol) in THF was cooled to 0° C. to 5° C. A solution of ethyl magnesium chloride in THF (2 M, 300 mL, 1.6 eq) was added dropwise maintaining an internal temperature below 10° C. The reaction mixture was stirred at 15° C. to 20° C. for 2 to 4 hours. Then carbon dioxide gas (58 g, 3.5 eq) was introduced subsurface at 0° C. to 5° C. after passing through concentrated sulfuric acid (50 mL). The reaction mixture was stirred at 0° C. to 5° C. for 2 hours and an 8% aqueous sodium chloride solution (601 g) was added dropwise at below 10° C., followed by addition of 37% aqueous HCl solution (92.5 g) at below 0° C.

The reaction mixture was stirred at 10° C. to 15° C. for 30 minutes then the stirring was stopped and after 30 minutes the phases were separated. The organic layer was concentrated to about 370 mL under vacuum, followed by three iterations of THF (1850 mL) addition and concentration under vacuum to about 370 mL to 555 mL. After confirming the reaction mixture was dry, three cycles of acetonitrile (925 mL) addition followed by vacuum concentration to about 555 mL to 740 mL were performed. The reaction mixture was heated to 75° C. and gradually cooled to 50° C. over one hour. Product seeds (1.85 g) were added at 50° C.

and the reaction mixture was stirred at 50° C. for 30 minutes. The batch was gradually cooled to −10° C. over three hours and kept at −10° C. for two hours. The batch was filtered and the cake was washed with cold acetonitrile (93 to 185 mL). 110 g of the title compound was obtained after drying the wet cake at 50° C. under vacuum for 12 hours. The product was evaluated by chiral HPLC which indicated >99.9% S-isomer.

Above-referenced product seeds were prepared as follows. A solution of (5S)-3-(5-bromo-4-methyl-2-thienyl)-5-(3,4,5-trichlorophenyl)-5-(trifluoromethyl)-4H-isoxazole (48.93 g, 99.1 mmol) in 300 ml of THF was cooled to 0° C. to 5° C. A solution of ethyl magnesium chloride in THF (2 M, 80 mL) was added dropwise maintaining an internal temperature below 10° C. The reaction mixture was stirred at 15° C. to 20° C. for 2 to 4 hours. Then carbon dioxide gas (25 g, 3.5 eq) was introduced subsurface at 0° C. to 5° C. after passing through concentrated sulfuric acid (50 mL). The reaction mixture was stirred at 0° C. to 5° C. for 6 hours and an 5% aqueous sodium chloride solution (157 g) was added dropwise at below 10° C., followed by addition of 37% aqueous HCl solution (25 g) at below 0° C. The reaction mixture was stirred at 10° C. to 15° C. for 30 minutes then the stirring was stopped and after 30 minutes the phases were separated. The organic layer was concentrated to remove the solvent. 50 ml of heptane was added into the mixture then removed the solvent. The crude product was dissolved in 50 ml of EA and 100 ml of heptane at 40° C. Additional 1000 ml of heptane was charged dropwise into the mixture slowly. Then the mixture was stirred at 40° C. for 15 h. The mixture was filtered and the wet cake was obtained. The wet cake was slurried by acetone at 20° C. The mixture was filter and the wet cake was dried at 50° C. under vacuum for 3 h to afford 9.7 g of product. The product was evaluated by chiral HPLC which indicated >99.9% S-isomer.

Example 6

3-Methyl-N-[2-oxo-2-(2,2,2-trifluoroethylamino)ethyl]-5-[(5S)-5-(3,4,5-trichlorophenyl)-5-(trifluoromethyl)-4H-isoxazol-3-yl]thiophene-2-carboxamide

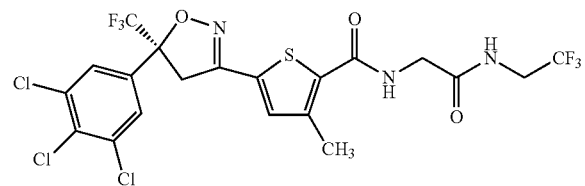 [SMILES: Cc1cc(C2=NO[C@@](c3cc(Cl)c(Cl)c(Cl)c3)(C(F)(F)F)C2)sc1C(=O)NCC(=O)NCC(F)(F)F]

A solution of 3-methyl-5-[(5S)-5-(3,4,5-trichlorophenyl)-5-(trifluoromethyl)-4H-isoxazol-3-yl]thiophene-2-carboxylic acid (101.5 g, 221.3 mmol) in DCM (1000 mL) was heated to 40° C. Thionyl chloride (50 g, 1.9 eq) was added dropwise and the reaction mixture was stirred at reflux for 2 to 4 hours. The reaction mixture was concentrated to 100 to 200 ml and DCM (500 mL) was added. Two more cycles of concentration followed by DCM addition were performed. In a separate vessel, a suspension of 2-amino-trifluoroethyl-acetamide HCl (50.26 g, 1.2 eq) in DCM (500 mL) was cooled to 0° C. to 5° C., triethylamine (70.15 g, 3.1 eq) was added, and the reaction mixture was stirred at 0° C. to 5° C. for 30 minutes. The acid chloride solution in DCM was then transferred to the reaction mixture containing 2-amino-trifluoroethyl-acetamide maintaining the internal temperature below 5° C. The reaction mixture was stirred at 0° C. to 5° C. for 2 to 4 hours. 1 N HCl (500 mL) was added dropwise and the reaction mixture was stirred at 15 to 25° C. for 30 minutes. The stirring was stopped and after 30 minutes the phases were separated. The organic layer was extracted with saturated sodium bicarbonate solution (1N, 1000 mL), the layers separated and the organic layer extracted with water (1000 mL). The layers were separated and the organic layer was concentrated under vacuum to 200 to 300 mL. Twice ethyl acetate (500 mL) was added and the batch was concentrated to 200 mL. The reaction mixture was heated to 55° C. and n-heptane (700 mL) was added dropwise at 55° C. Product seeds (1.0 g) were added and the reaction mixture was stirred at 55° C. for one hour. N-Heptane (1000 mL) was added dropwise and the mixture was stirred at 55° C. for three hours. The batch was gradually cooled to 35° C. over three hours, then to 20° C. over three hours. The batch was filtered and the cake was washed with n-heptane (200 mL). 113 g of the title compound was obtained after drying at 50° C. under vacuum for 12 hours. Above-referenced product seeds were prepared as follows. The crude product was dissolved in 7.9 wt-parts of cumene to obtain a solution at <150° C. Then 2.3 wt-parts of heptanes was added to the hot solution until slight haze was observed. The heating was turned off and the mixture was cooled to ambient temperature and stirred overnight. The desired polymorph G was obtained as powder after filtration and drying under vacuum, which was used as seeds to induce crystallization of polymorph G in future batches.

Example 7

3-Methyl-5-[(5S)-5-(3,4,5-trichlorophenyl)-5-(trifluoromethyl)-4H-isoxazol-3-yl]thiophene-2-carboxylic acid

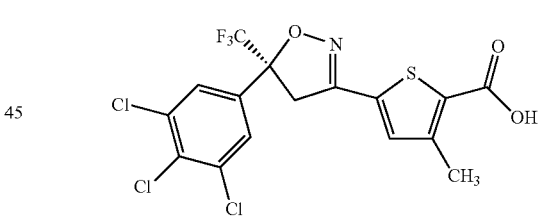

Combined 2-bromo-3-methyl-5-acetylthiophene (20 g), p-toluenesulphonic acid monohydrate (2.3 g), and ethylene glycol (11.3 g) in toluene (120 mL) and heated with stirring at 115° C. for 12 hours as water was collected with the Dean-Stark trap. The reaction mixture was then cooled and quenched with saturated aqueous sodium bicarbonate solution (40 mL). The organic layer was separated and washed twice with water (40 mL) and concentrated at 60° C. under vacuum to give 2-(5-bromo-4-methyl-2-thienyl)-2-methyl-1,3-dioxolane.

Combined 2-(5-bromo-4-methyl-2-thienyl)-2-methyl-1,3-dioxolane (25.2 g) and THF (50 mL) and cooled in an ice/water bath. With stirring ethylmagnesium chloride in THF (2.0 M, 75 mL) was added while maintaining the temperature at 10° C. to 30° C. with an ice/water bath. The reaction mixture was then warmed to ambient temperature. After 90 minutes, the reaction mixture was cooled with an ice/water bath to 0° C. to 5° C. and a gaseous carbon dioxide was bubbled into the reaction, subsurface, at 5° C. to 14° C. for 30 minutes. The reaction mixture was allowed to warm to ambient temperature and stirred overnight. The reaction mixture was cooled to 0° C. to 10° C. and 75 mL saturated aqueous brine solution was added at 10° C. to 35° C. The pH was then adjusted to about pH 1 with 37% aqueous HCl. Ethyl acetate (50 mL) and water (25 mL) were added and the reaction mixture was stirred. The aqueous layer was separated and the organic layer was washed with saturated aqueous brine (3×50 mL). The washed organic layer was concentrated at 40° C. under vacuum to give 3-methyl-5-(2-methyl-1,3-dioxolan-2-yl)thiophene-2-carboxylic acid (19.2 g) as a red oily product which solidified during storage at ambient temperature. MS: ESI+ 228.96; ESI−: 226.98.

Combined 3-methyl-5-(2-methyl-1,3-dioxolan-2-yl)thiophene-2-carboxylic acid (19.2 g), potassium carbonate (24.9 g) and 60 mL of dimethylformamide (DMF). The reaction mixture was cooled to 0-5° C. with an ice/water bath and methyl iodide (13.1 mL) was then added dropwise while maintaining the temperature at 0-5° C. The reaction mixture was stirred at ambient temperature for 1 hour before being cooled to 0° C. to 10° C. and quenched with water (180 mL) and ethyl acetate (180 mL). The aqueous layer was separated and the organic layer was washed with water (2×60 mL) and aqueous brine (60 mL). The organic layer was then evaporated at 40° C. under vacuum to give methyl 3-methyl-5-(2-methyl-1,3-dioxolan-2-yl)thiophene-2-carboxylate (21.3 g) as a red oil product. MS: ESI+ 243.00.

p-Toluenesulphonic acid monohydrate (1.7 g), methyl 3-methyl-5-(2-methyl-1,3-dioxolan-2-yl)thiophene-2-carboxylate (21.3 g), acetone (140 mL) and water (14 mL) were combined and stirred at 35° C. for 2 hours and then cooled to 20° C. Then sodium bicarbonate (1.5 g) was added and the reaction mixture was stirred at 20° C. for 10 minutes. The mixture was then concentrated at 40° C. under vacuum to give a residue. The residue was dissolved with 200 ml ethyl acetate and washed with water (50 mL). The layers were separated and the organic layer was washed with water (2×50 mL). The organic layer was concentrated at 40° C. under vacuum to give a residue which was purified by flash chromatography with a mixture of MTBE in n-heptane (0-15% v/v) to give methyl 5-acetyl-3-methyl-thiophene-2-carboxylate (4.9 g). $^1$H NMR (500 MHz, CDCl$_3$) δ ppm 2.51 (d, J=5.87 Hz, 6H) 3.85 (s, 3H) 7.43 (s, 1H). 13C NMR (126 MHz, CDCl$_3$) δ ppm 15.85 (s, 1 C) 26.80 (s, 1 C) 52.06 (s, 1 C) 76.74 (s, 1 C) 77.00 (s, 1 C) 77.26 (s, 1 C) 132.65 (s, 1 C) 135.25 (s, 1 C) 145.37 (s, 1 C) 146.02 (s, 1 C) 162.57 (s, 1 C) 190.78 (s, 1 C).

Combined methyl 5-acetyl-3-methyl-thiophene-2-carboxylate (4.1 g), 2,2,2-trifluoro-1-(3,4,5-trichlorophenyl) ethanone (5.74 g), triethylamine (8.4 mL) and MTBE (41 mL) and heated the reaction mixture at about 57° C. After 3 hours, the reaction mixture was cooled to ambient temperature and stirred for 12 hours. The reaction mixture was then cooled to 0-5° C. and thionyl chloride (2.3 mL) was added dropwise while maintaining the temperature at 0-10° C. The reaction mixture was then warmed to ambient temperature and stirred overnight. The mixture was then diluted with MTBE (45 mL) and cooled to 0-5° C. A mixture of saturated aqueous sodium bicarbonate (45 mL) and water (45 mL) was added dropwise. The reaction mixture was then combined with ethyl acetate (60 mL) and the layers were separated. The aqueous layer was extracted with ethyl acetate (41 mL) and the organic layers were combined and washed with aqueous brine (2×40 mL). The organic layer was then evaporated under vacuum at 30° C. to 40° C. to give a residue. The residue was suspended in ethanol (50 mL), stirred for 1 hour and then cooled to 0° C. to 5° C. With stirring, water (50 mL) was added dropwise at 0° C. to 5° C. and the mixture was stirred for 3 hours to give a solid. The solid was collected by filtration, washed with precooled 1:3 ethanol/water mixture (2×10 mL) and dried under vacuum at 35° C. to 40° C. to give methyl 3-methyl-5-[(E/Z)-4,4,4-trifluoro-3-(3,4,5-trichlorophenyl)but-2-enoyl]thiophene-2-carboxylate (8.43 g) as a brown solid. E/Z ratio: 77:23 (by $^1$H NMR).

Combined methyl 3-methyl-5-[(E/Z)-4,4,4-trifluoro-3-(3,4,5-trichlorophenyl)but-2-enoyl]thiophene-2-carboxylate (500 mg), (R)-[(2S)-1-[[3,5-bis(trifluoromethyl)phenyl]methyl]-5-vinyl-quinuclidin-1-ium-2-yl]-(6-methoxy-4-quinolyl)methanol bromide (69 mg), and DCM (50 mL) and cooled to −10 to −15° C. A precooled mixture of aqueous sodium hydroxide (10 N, 0.33 mL) and aqueous hydroxyl amine (50%, 0.223 mL) was added dropwise via a syringe while maintaining the temperature at −10° C. to −15° C. After 5 hours, aqueous hydrochloric acid (2 N, 25 mL) was slowly added and the reaction mixture was then warmed to 10° to 15° C. The layers were then separated and the organic layer was washed with water (2×, 25 mL) and evaporated at 50° C. under vacuum to give methyl 3-methyl-5-[(5S)-5-(3,4,5-trichlorophenyl)-5-(trifluoromethyl)-4H-isoxazol-3-yl]thiophene-2-carboxylate (640 mg) which was taken to the next step without further purification.

Methyl 3-methyl-5-[(5S)-5-(3,4,5-trichlorophenyl)-5-(trifluoromethyl)-4H-isoxazol-3-yl]thiophene-2-carboxylate (640 mg) was sequentially twice combined with THF (5 mL) and evaporated to give a residue which was combined with THF (4.2 mL), water (1.6 mL), and aqueous sodium hydroxide (10 N, 0.22 mL). The reaction mixture was then heated to 60° C. with stirring. After 4 hours, the reaction mixture was evaporated to near dryness to give a residue which was partitioned between ethyl acetate (50 mL) and aqueous hydrochloric acid (0.5 N HCl, 25 mL). The layers were separated and the organic layer was washed with water (2×25 mL) and evaporated at 50° C. under vacuum to give a residue. The residue was combined with toluene (5 mL) and then evaporated at 60° C. under vacuum to give the title compound as a foamy solid (450 mg) S/R ratio: 89:11. $^1$H NMR (500 MHz, CDCl$_3$) δ ppm 2.53-2.60 (m, 3H) 3.63-3.73 (m, 1H) 4.03-4.12 (m, 1H) 7.12-7.14 (m, 1H) 7.60-7.65 (m, 2H).

Example 8

Methyl 3-methyl-5-[(5S)-5-(3,4,5-trichlorophenyl)-5-(trifluoromethyl)-4H-isoxazol-3-yl]thiophene-2-carboxylate

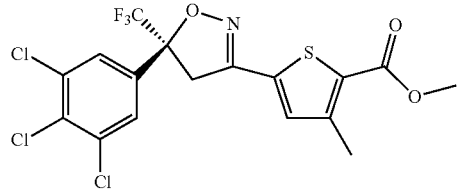 [SMILES: COC(=O)c1sc(C2=NO[C@@](c3cc(Cl)c(Cl)c(Cl)c3)(C(F)(F)F)C2)cc1C]

Combined 3-methyl-2-thiophenecarboxylic acid (2.5 g) and THF (5 mL) at ambient temperature and then added 2,2,6,6-tetramethylpiperidinylmagnesium chloride lithium chloride complex (50 mL 0.94 M in THF) via a syringe over 15 minutes while controlling temperature at less than 45° C. The reaction mixture was stirred at 25° C. for 1 hour and then N-methoxy-N-methylacetamide (5.0 mL) was added via a syringe while controlling the temperature at less than 40° C. After stirring at ambient temperature for about 90 minutes, the reaction mixture was cooled to 0-5° C. and aqueous hydrochloric acid (2M, 100 mL) was added while controlling the temperature at less than 45° C. MTBE (100 mL) was added, the layers were separated and the aqueous layer was extracted with MTBE (50 mL). The combined organic layers were washed with aqueous brine (2×25 mL) and then evaporated at 45° C. under vacuum to give 5-acetyl-3-methyl-thiophene-2-carboxylic acid (4.8 g) as a yellow solid.

5-Acetyl-3-methyl-thiophene-2-carboxylic acid (4.8 g) was combined with potassium carbonate (3.0 eq) and DMF (30 mL) and then methyl iodide (2.5 eq) was then added dropwise. After 45 minutes, water (90 mL) and MTBE (120 mL) were added with mixing and then the layers were separated and the aqueous layer was extracted with MTBE (60 mL). The combined organic layers were washed with water (2×30 mL) and then evaporated at 55° C. under vacuum to give methyl 5-acetyl-3-methyl-thiophene-2-carboxylate (4.5 g).

Combined methyl 5-acetyl-3-methyl-thiophene-2-carboxylate (4.5 g), 2,2,2-trifluoro-1-(3,4,5-trichlorophenyl) ethanone (3.66 g), triethylamine (2.9 mL) and MTBE (30 mL) and heated the reaction mixture at about 60° C. After 6.5 hours, additional triethylamine (2.0 mL) was added and heating was continued at 60° C. for 3 hours. The reaction mixture was cooled to 0° C. to 5° C. and thionyl chloride (1.7 mL) was added dropwise while maintaining the temperature at less than 12° C. The reaction mixture was then warmed to ambient temperature and stirred 1 hour before being diluted with MTBE (30 mL) and then cooled to 10° C. followed by the slow addition of a mixture of saturated aqueous sodium bicarbonate (30 mL) and water (30 mL). The layers were then separated and the aqueous layer was extracted with MTBE (30 mL). The combined organic layers were washed with aqueous brine (2×30 mL) and then evaporated under vacuum at 30° C. to 40° C. to give a residue. The residue was twice suspended in ethanol (30 mL) and evaporated to near dryness. The residue was then suspended in ethanol (30 mL) and stirred for 1 hour at 0° C. to 5° C. to give a solid. The solid was collected by filtration, washed with precooled 1:3 ethanol/water mixture (2×10 mL) and dried under vacuum at 40° C. to give methyl 3-methyl-5-[(E/Z)-4,4,4-trifluoro-3-(3,4,5-trichlorophenyl) but-2-enoyl]thiophene-2-carboxylate (2.54 g), nearly pure E isomer (by $^1$H NMR).

Combined methyl 3-methyl-5-[(E/Z)-4,4,4-trifluoro-3-(3,4,5-trichlorophenyl)but-2-enoyl]thiophene-2-carboxylate (500 mg), (R)-[(2S)-1-[[3,5-bis(trifluoromethyl)phenyl]methyl]-5-vinyl-quinuclidin-1-ium-2-yl]-(6-methoxy-4-quinolyl)methanol bromide (69 mg), and DCM (50 mL) and cooled to −10 to −15° C. A precooled mixture aqueous of sodium hydroxide (10 N, 0.33 mL) and aqueous hydroxyl amine (50%, 0.223 mL) was added dropwise via a syringe with stirring while maintaining the temperature at −10° C. to −15° C. After 5 hours at −10° C. to −15° C. the mixture was analyzed. S/R ratio: 89:11.

Example 9

Methyl 3-methyl-5-[(5S)-5-(3,4,5-trichlorophenyl)-5-(trifluoromethyl)-4H-isoxazol-3-yl]thiophene-2-carboxylate Combined methyl 3-methyl-5-[(E/Z)-4,4,4-trifluoro-3-(3,4,5-trichlorophenyl)but-2-enoyl]thiophene-2-carboxylate (500 mg), (R)-[(2S)-1-[[3,5-bis(trifluoromethyl)phenyl]methyl]-5-vinyl-quinuclidin-1-ium-2-yl]-(6-methoxy-4-quinolyl)methanol bromide (69 mg), and toluene/methyl cyclohexane (1:1 (v/v) 50 mL) and cooled to −10° C. to −15° C. A precooled mixture of aqueous sodium hydroxide (10 N, 0.33 mL) and aqueous hydroxyl amine (50%, 0.223 mL) was added dropwise via a syringe with stirring while maintaining the temperature at −10° C. to −15° C. After 46 hours at −10° C. to −15° C. the mixture was analyzed. S/R ratio: 92:8.

Example 10

Methyl 3-methyl-5-[(E/Z)-4,4,4-trifluoro-3-(3,4,5-trichlorophenyl)but-2-enoyl]thiophene-2-carboxylate

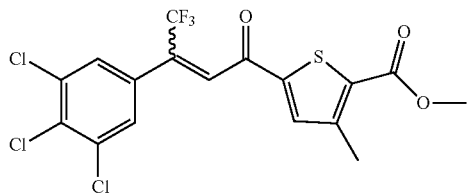 [SMILES: COC(=O)c1sc(C(=O)C=C(c2cc(Cl)c(Cl)c(Cl)c2)C(F)(F)F)cc1C]

Combined methyl 3-methyl-5-[(E/Z)-4,4,4-trifluoro-3-(3,4,5-trichlorophenyl)but-2-enoyl]thiophene-2-carboxylate (500 mg), (R)-[(2S)-1-[[3,5-bis(t-butyl)phenyl]methyl]-5-vinyl-quinuclidin-1-ium-2-yl]-(6-methoxy-4-quinolyl) methanol bromide (69 mg), and DCM (50 mL) and cooled to −10 to −15° C. A precooled mixture of aqueous sodium hydroxide (10 N, 0.33 mL) and aqueous hydroxyl amine (50%, 0.223 mL) was added dropwise via a syringe with stirring while maintaining the temperature at −10° C. to −15° C. After 18 hours at −10° C. to −15° C. the mixture was analyzed. S/R ratio: 81:19.

Example 11

Methyl 3-methyl-5-[(E/Z)-4,4,4-trifluoro-3-(3,4,5-trichlorophenyl)but-2-enoyl]thiophene-2-carboxylate Combined methyl 3-methyl-5-[(E/Z)-4,4,4-trifluoro-3-(3,4,5-trichlorophenyl)but-2-enoyl]thiophene-2-carboxylate (500 mg), (R)-[(2S)-1-[[3,5-bis(t-butyl)phenyl]methyl]-5-vinyl-quinuclidin-1-ium-2-yl]-(6-methoxy-4-quinolyl) methanol bromide (69 mg), and DIPE (50 mL) and cooled to −10 to −15° C. A precooled mixture of aqueous sodium hydroxide (10 N, 0.33 mL) and aqueous hydroxyl amine (50%, 0.223 mL) was added dropwise via a syringe with stirring while maintaining the temperature at −10° C. to −15° C. After 18 hours at −10° C. to −15° C. the mixture was analyzed. S/R ratio: 88:12.

Example 12

Methyl 3-methyl-5-[(E/Z)-4,4,4-trifluoro-3-(3,4,5-trichlorophenyl)but-2-enoyl]thiophene-2-carboxylate Combined methyl 3-methyl-5-[(E/Z)-4,4,4-trifluoro-3-(3,4,5-trichlorophenyl)but-2-enoyl]thiophene-2-carboxylate (500 mg), (R)-[(2S)-1-[[3,5-bis(t-butyl)phenyl]methyl]-5-vinyl-quinuclidin-1-ium-2-yl]-(6-methoxy-4-quinolyl) methanol bromide (69 mg), and diisopropyl ether (40 mL) and DCM (10 mL) and cooled to −10 to −15° C. A precooled mixture of aqueous sodium hydroxide (10 N, 0.33 mL) and aqueous hydroxyl amine (50%, 0.223 mL) was added dropwise via a syringe with stirring while maintaining the temperature at −10° C. to −15° C. After 18 hours at −10° C. to −15° C. the mixture was analyzed. S/R ratio: 91:9.

For reasons of completeness, various aspects of the disclosure are set out in the following numbered clauses.

Clause 1. A process for making an enantiomerically pure isoxazoline compound of formula (1), wherein $R_5$ is a $C_1$-$C_4$ aliphatic chain which optionally contains a double or triple bond, wherein the chain is optionally substituted with 1 to 5 substituents independently selected from the group consisting of halogen, cyano, nitro, hydroxyl, oxo, $C_3$-$C_6$ cycloalkyl, $C_1$-$C_4$ alkoxy, $C_1$-$C_7$ aminocarbonyl, —N($C_1$-$C_4$ alkyl)$_2$, —S$C_1$-$C_4$ alkyl, —S(O)$C_1$-$C_4$ alkyl, and —SO$_2C_1$-$C_4$ alkyl, comprising the steps of:

(i) reacting a compound of formula (2) with hydroxylamine wherein X is selected from the group consisting of halogen and —C(O)OR$_4$ wherein $R_4$ is a $C_1$-$C_4$ alkyl and an appropriate base and a compound of formula (3) wherein Y is an anion, $R_1$ is selected from the group consisting of hydrogen and methoxy, $R_2$ is selected from the group consisting of ethyl and vinyl, $R_3$ is selected from the group consisting of aryl optionally substituted with 1 to 5 substituents independently selected from the group consisting of nitro, halogen, amino, trifluoromethyl, $C_1$-$C_4$ alkyl, $C_1$-$C_4$ alkoxy, and benzyloxy, and heteroaryl optionally substituted with 1 to 3 substituents independently selected from the group consisting of halogen, trifluoromethyl, $C_1$-$C_4$ alkyl, and $C_1$-$C_4$ alkoxy, to give a compound of formula (4);

(ii) converting X of a compound of formula (4) to a carboxylic acid of the compound of formula (5);

(iii) optionally crystallizing the compound of formula (5) with a solvent selected from the group consisting of $C_{1-5}$ alcohol, $C_{2-5}$ alkyl cyanide, $C_{3-9}$ alkyl ketone, $C_{2-8}$ alkyl ether, $C_{2-8}$ alkyl acetate, and optionally with an anti-solvent selected from the group consisting of water and $C_{5-8}$ hydrocarbon, and (iv) coupling the compound of formula 5 with an appropriate amine.

Clause 2. A process according to clause 1, wherein the appropriate amine is a compound of formula (6), wherein $R_5$ is a $C_1$-$C_4$ aliphatic chain which optionally contains a double or triple bond, wherein the chain is optionally substituted with 1 to 5 substituents independently selected from the group consisting of halogen, cyano, nitro, hydroxyl, oxo, $C_3$-$C_6$ cycloalkyl, $C_1$-$C_4$ alkoxy, $C_1$-$C_7$ aminocarbonyl, —N($C_1$-$C_4$ alkyl)$_2$, —S$C_1$-$C_4$ alkyl, —S(O)$C_1$-$C_4$ alkyl, and —SO$_2C_1$-$C_4$ alkyl.

Clause 3. A process according to clause 2, wherein $R_5$ is $C_3$ alkyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, $C_1$-$C_7$ aminocarbonyl, —N($C_1$-$C_4$ alkyl)$_2$, —S$C_1$-$C_4$ alkyl, —S(O)$C_1$-$C_4$ alkyl, and —SO$_2C_1$-$C_4$ alkyl.

Clause 4. A process according to clause 2, wherein $R_5$ is ethyl optionally substituted with 1 to 5 substituents independently selected from the group consisting of halogen, cyano, nitro, hydroxyl, oxo, $C_3$-$C_6$ cycloalkyl, $C_1$-$C_4$ alkoxy, $C_1$-$C_7$ aminocarbonyl, —N($C_1$-$C_4$ alkyl)$_2$, —S$C_1$-$C_4$ alkyl, —S(O)$C_1$-$C_4$ alkyl, and —SO$_2C_1$-$C_4$ alkyl.

Clause 5. A process according to clause 2, wherein $R_5$ is methyl optionally substituted with 1 to 3 substituents independently selected from the group consisting of halogen, cyano, nitro, hydroxyl, oxo, $C_3$-$C_6$ cycloalkyl, $C_1$-$C_4$ alkoxy, $C_1$-$C_7$ aminocarbonyl, —N($C_1$-$C_4$ alkyl)$_2$, —S$C_1$-$C_4$ alkyl, —S(O)$C_1$-$C_4$ alkyl, and —SO$_2C_1$-$C_4$ alkyl.

Clause 6. A process according to clause 2 or 4, wherein $R_5$ is ethyl substituted with 1, 2, or 3 substituents independently selected from the group consisting of halogen, cyano, nitro, hydroxyl, oxo, $C_3$-$C_6$ cycloalkyl, $C_1$-$C_4$ alkoxy, $C_1$-$C_7$ aminocarbonyl, —N($C_1$-$C_4$ alkyl)$_2$, —S$C_1$-$C_4$ alkyl, —S(O)$C_1$-$C_4$ alkyl, and —SO$_2C_1$-$C_4$ alkyl.

Clause 7. A process according to any one of clauses 2, 4, and 6, wherein $R_5$ is ethyl substituted with 1, 2, or 3 halogen substituents.

Clause 8. A process according to any one of clauses 2, 4, 6, and 7, wherein $R_5$ is ethyl substituted with 1 halogen substituent.

Clause 9. A process according to any one of clauses 2, 4, 6, and 7, wherein $R_5$ is ethyl substituted with 2 halogen substituents.

Clause 10. A process according to any one of clauses 2, 4, 6, and 7, wherein $R_5$ is ethyl substituted with 3 halogen substituents.

Clause 11. A process according to any one of clauses 2, 4, and 6-8, wherein $R_5$ is ethyl substituted with 1 fluoro substituent.

Clause 12. A process according to any one of clauses 2, 4, 6, 7, and 9, wherein $R_5$ is ethyl substituted with 2 fluoro substituents.

Clause 13. A process according to any one of clauses 2, 4, 6, 7, and 10, wherein $R_5$ is ethyl substituted with 3 fluoro substituents.

Clause 14. A process according to any one of clauses 1, 2, 4, 6, 7, 10, and 13, wherein the appropriate amine is 2-amino-2',2',2'-trifluoroethyl-acetamide.

Clause 15. A process according to clause 1, wherein the appropriate amine is the sequential reaction of glycine optionally carboxyl protected, followed by deprotection if necessary and then by coupling with 2,2,2-trifluorethylamine.

Clause 16. A process for making an enantiomerically pure compound of formula (5) comprising the steps of (i) reacting a compound of formula (2) with hydroxylamine wherein X is selected from the group consisting of halogen and —C(O)OR$_4$ wherein $R_4$ is a $C_1$-$C_4$ alkyl and an appropriate base and a compound of formula (3) wherein Y is an anion, $R_1$ is selected from the group consisting of hydrogen and methoxy, $R_2$ is selected from the group consisting of ethyl and vinyl, $R_3$ is selected from the group consisting of aryl optionally substituted with 1 to 5 substituents independently selected from the group consisting of nitro, halogen, amino, trifluoromethyl, $C_1$-$C_4$ alkyl, $C_1$-$C_4$ alkoxy, and benzyloxy, and heteroaryl optionally substituted with 1 to 3 substituents independently selected from the group consisting of halogen, trifluoromethyl, $C_1$-$C_4$ alkyl, and $C_1$-$C_4$ alkoxy, to give a compound of formula (4);

(ii) converting X of a compound of formula (4) to a carboxylic acid of the compound of formula (5);

(iii) optionally crystallizing the compound of formula (5) with a solvent selected from the group consisting of $C_{1-5}$ alcohol, $C_{2-5}$ alkyl cyanide, $C_{3-9}$ alkyl ketone, $C_{2-8}$ alkyl ether, $C_{2-8}$ alkyl acetate, and optionally with an anti-solvent selected from the group consisting of water and $C_{5-8}$ hydrocarbon.

Clause 17. A process according to any one of clauses 1 to 16 wherein X is halogen.

Clause 18. A process according to clause 17 wherein X is bromo.

Clause 19. A process according to clause 18 wherein X is chloro.

Clause 20. A process according to any one of clauses 1 to 16 wherein X is —C(O)OR$_4$ wherein R$_4$ is C$_1$-C$_4$ alkyl.

Clause 21. A process according to clause 20 wherein R$_4$ is methyl.

Clause 22. A process according to clause 20 wherein R$_4$ is ethyl.

Clause 23. A process of any one of clauses 1 to 22 wherein R$_1$ is methoxy.

Clause 24. The process of any one of clauses 1-23, wherein step (i) is conducted at a temperature from −40° C. to −10° C.

Clause 25. The process of any one of clauses 1-23, wherein step (i) is conducted at a temperature from −30° C. to −20° C.

Clause 26. The process of any one of clauses 1-23, wherein step (i) is conducted at a temperature of about −30° C.

Clause 27. The process of any one of clauses 1-26, wherein the reaction of the compound of formula (2) with hydroxylamine, the appropriate base, and the compound of formula (3) is conducted in the presence of a solvent system comprising dichloromethane and an ether.

Clause 28. The process of clause 27, wherein the ether is methyl t-butyl ether, ethyl t-butyl ether, diisopropyl ether, or t-amyl methyl ether.

Clause 29. The process of clause 27, wherein the ether is methyl t-butyl ether or ethyl t-butyl ether.

Clause 30. The process of any one of clauses 1-29, wherein the enantiomeric excess of the compound of formula (4) is greater than or equal to 80%.

Clause 31. The process of any one of clauses 1-29, wherein the enantiomeric excess of the compound of formula (4) is greater than or equal to 93%.

Clause 32. The process of any one of clauses 1-31, wherein step (iii) occurs.

Clause 33. The process of clause 32, wherein the anti-solvent in (iii) is present.

Clause 34. The process of clause 32 or 33, wherein the solvent in (iii) is C$_{1-5}$ alcohol.

Clause 35. The process of clause 32 or 33, wherein the solvent in (iii) is C$_{2-5}$ alkyl cyanide.

Clause 36. The process of clause 32 or 33, wherein the solvent in (iii) is C$_{3-9}$ alkyl ketone.

Clause 37. The process of clause 32 or 33, wherein the solvent in (iii) is C$_{2-8}$ alkyl ether.

Clause 38. The process of clause 32 or 33, wherein the solvent in (iii) is C$_{2-8}$ alkyl acetate.

Clause 39. The process of clause 34, wherein the C$_{1-5}$ alcohol in (iii) is isopropanol.

Clause 40. The process of clause 34, wherein the C$_{1-5}$ alcohol in (iii) is ethanol.

Clause 41. The process of clause 35, wherein the C$_{2-5}$ alkyl cyanide in (iii) is acetonitrile.

Clause 42. The process of clause 36, wherein the C$_{3-9}$ alkyl ketone in (iii) is acetone.

Clause 43. The process of clause 36, wherein the C$_{3-9}$ alkyl ketone in (iii) is methyl ethyl ketone.

Clause 44. The process of clause 37, wherein the C$_{2-8}$ alkyl ether in (iii) is tetrahydrofuran.

Clause 45. The process of clause 37, wherein the C$_{2-8}$ alkyl ether in (iii) is 2-methyltetrahydrofuran.

Clause 46. The process of clause 38, wherein the C$_{2-8}$ alkyl acetate in (iii) is ethyl acetate.

Clause 47. The process of clause 38, wherein the C$_{2-8}$ alkyl acetate in (iii) is isopropyl acetate.

Clause 48. The process of any one of clauses 32 to 47, wherein the anti-solvent in (iii) is water.

Clause 49. The process of any one of clauses 32 to 47, wherein the anti-solvent in (iii) is C$_{5-8}$ hydrocarbon.

Clause 50. The process of clause 49, wherein the C$_{5-8}$ hydrocarbon is pentane.

Clause 51. The process of clause 49, wherein the C$_{5-8}$ hydrocarbon is hexane.

Clause 52. The process of clause 49, wherein the C$_{5-8}$ hydrocarbon is heptane.

Clause 53. The process of clause 49, wherein the C$_{5-8}$ hydrocarbon is cyclohexane.

Clause 54. The process of clause 49, wherein the C$_{5-8}$ hydrocarbon is methylcyclohexane.

Clause 55. The process of any one of clauses 1-54, wherein the enantiomeric excess of the compound of formula (5) is greater than or equal to 90%.

Clause 56. The process of any one of clauses 1-54, wherein the enantiomeric excess of the compound of formula (5) is greater than or equal to 96%.

Clause 57. The process of any one of clauses 1-54, wherein the enantiomeric excess of the compound of formula (5) is greater than or equal to 98%.

Clause 58. The process of any one of clauses 1-54, wherein the enantiomeric excess of the compound of formula (5) is greater than or equal to 99%.

Clause 59. The process of any one of clauses 1-54, wherein the enantiomeric excess of the compound of formula (5) is greater than or equal to 99.6%.

Clause 60. A process for improving the enantiomeric purity of 3-methyl-5-[(5S)-5-(3,4,5-trichlorophenyl)-5-(trifluoromethyl)-4H-isoxazol-3-yl]thiophene-2-carboxylic acid comprising: crystallization from a solvent selected from the group consisting of C$_{1-5}$ alcohol, C$_{2-5}$ alkyl cyanide, C$_{3-9}$ alkyl ketone, C$_{2-8}$ alkyl ether, C$_{2-8}$ alkyl acetate, and optionally with an anti-solvent selected from the group consisting of water and C$_{5-8}$ hydrocarbon.

Clause 61. The process of clause 60, wherein the anti-solvent is present.

Clause 62. The process of clause 60 or 61, wherein the solvent is C$_{1-5}$ alcohol.

Clause 63. The process of clause 60 or 61, wherein the solvent is C$_{2-5}$ alkyl cyanide.

Clause 64. The process of clause 60 or 61, wherein the solvent is C$_{3-9}$ alkyl ketone.

Clause 65. The process of clause 60 or 61, wherein the solvent is C$_{2-8}$ alkyl ether.

Clause 66. The process of clause 60 or 61, wherein the solvent is C$_{2-8}$ alkyl acetate.

Clause 67. The process of clause 62, wherein the C$_{1-5}$ alcohol is isopropanol.

Clause 68. The process of clause 62, wherein the C$_{1-5}$ alcohol is ethanol.

Clause 69. The process of clause 63, wherein the C$_{2-5}$ alkyl cyanide is acetonitrile.

Clause 70. The process of clause 64, wherein the C$_{3-9}$ alkyl ketone is acetone.

Clause 71. The process of clause 64, wherein the C$_{3-9}$ alkyl ketone is methyl ethyl ketone.

Clause 72. The process of clause 65, wherein the C$_{2-8}$ alkyl ether is tetrahydrofuran.

Clause 73. The process of clause 65, wherein the C$_{2-8}$ alkyl ether is 2-methyltetrahydrofuran.

Clause 74. The process of clause 66, wherein the C$_{2-8}$ alkyl acetate is ethyl acetate.

Clause 75. The process of clause 66, wherein the C$_{2-8}$ alkyl acetate is isopropyl acetate.

Clause 76. The process of any one of clauses 60 to 75, wherein the anti-solvent is water.

Clause 77. The process of any one of clauses 60 to 75, wherein the anti-solvent is $C_{5-8}$ hydrocarbon.

Clause 78. The process of clause 77, wherein the $C_{5-8}$ hydrocarbon is pentane.

Clause 79. The process of clause 77, wherein the $C_{5-8}$ hydrocarbon is hexane.

Clause 80. The process of clause 77, wherein the $C_{5-8}$ hydrocarbon is heptane.

Clause 81. The process of clause 77, wherein the $C_{5-8}$ hydrocarbon is cyclohexane.

Clause 82. The process of clause 77, wherein the $C_{5-8}$ hydrocarbon is methylcyclohexane.

Clause 83. The process of any one of clauses to 60 to 82, wherein the enantiomeric purity of the crystallized 3-methyl-5-[(5S)-5-(3,4,5-trichlorophenyl)-5-(trifluoromethyl)-4H-isoxazol-3-yl]thiophene-2-carboxylic acid is 98% or greater.

Clause 88. The process of any one of clauses 60 to 82, wherein the enantiomeric purity of the crystallized 3-methyl-5-[(5S)-5-(3,4,5-trichlorophenyl)-5-(trifluoromethyl)-4H-isoxazol-3-yl]thiophene-2-carboxylic acid is 99% or greater.

Clause 89. The process of any one of clauses 60 to 82, wherein the enantiomeric purity of the crystallized 3-methyl-5-[(5S)-5-(3,4,5-trichlorophenyl)-5-(trifluoromethyl)-4H-isoxazol-3-yl]thiophene-2-carboxylic acid is 99.8% or greater.

Clause 90. A composition comprising an isoxazoline compound of formula (1) in 98% or greater enantiomeric purity.

Clause 91. A composition comprising an isoxazoline compound of formula (1) in 99% or greater enantiomeric purity.

Clause 92. A composition comprising an isoxazoline compound of formula (1) in 99.8% or greater enantiomeric purity.

Clause 93. A method of treating or preventing flea infestations, comprising administering a therapeutically effective amount to a patient in need thereof the composition of clause 90.

Clause 94. A method of treating or preventing flea infestations, comprising administering a therapeutically effective amount to a patient in need thereof the composition of clause 91.

Clause 95. A method of treating or preventing flea infestations, comprising administering a therapeutically effective amount to a patient in need thereof the composition of clause 92.

Clause 96. The method of any one of clauses 93-95, wherein the patient is a dog.

Clause 97. The method of any one of clauses 93-95, wherein the patient is a cat.

Clause 98. The composition of any one of clauses 90-92, wherein the isoxazoline compound of formula (1) is lotilaner.

Clause 99. The method of any one of clauses 93-97, wherein the isoxazoline compound of formula (1) is lotilaner.

Clause 100. The process of any one of clauses 1-59, wherein the appropriate base is selected from the group consisting of lithium hydroxide, sodium hydroxide, potassium hydroxide, barium hydroxide, cesium hydroxide, sodium phosphate, potassium phosphate, sodium methoxide, potassium hydroxide, potassium t-butoxide, and mixtures thereof.

Clause 101. The process of any one of clauses 1-59, wherein Y is selected from the group consisting of tosylate, brosylate, mesylate, nosylate, triflate, acetate, halide, sulfate, phosphate, hydroxide, and boron tetrafluoride.

Clause 102. The process of any one of clauses 1-59 and 101, wherein Y is halide.

Clause 103. The process of any one of clauses 1-59, 101, and 102, wherein Y is chloride.

Clause 104. The process of any one of clauses 1-59, 101, and 102, wherein Y is bromide.

The invention claimed is:

1. A process for making an isoxazoline compound of formula (1)

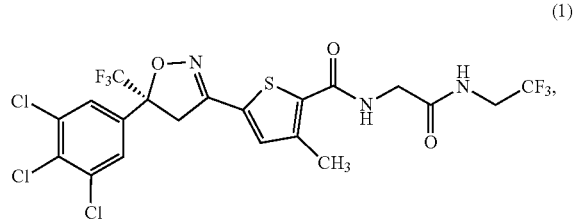 [SMILES: Cc1cc(C2=NO[C@@](c3cc(Cl)c(Cl)c(Cl)c3)(C(F)(F)F)C2)sc1C(=O)NCC(=O)NCC(F)(F)F]

(1)

comprising (i) reacting a compound of formula (2)

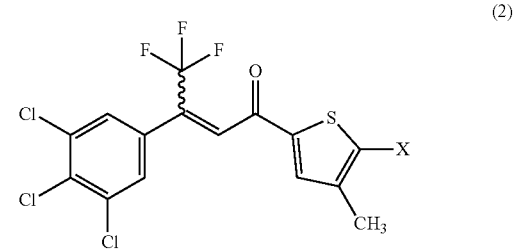

(2)

with hydroxylamine, sodium hydroxide and a compound of formula (3), wherein the base is;

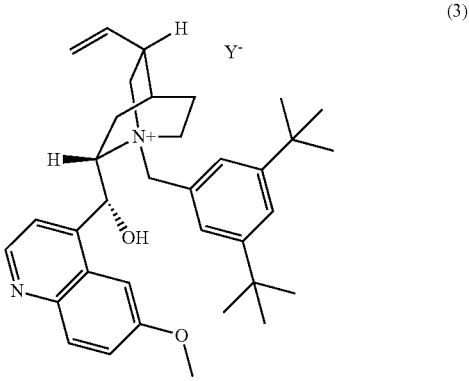

(3)

wherein Y⁻ is a halide, wherein the halide is selected from the group consisting of bromide and chloride, to give a compound of formula (4)

(4)

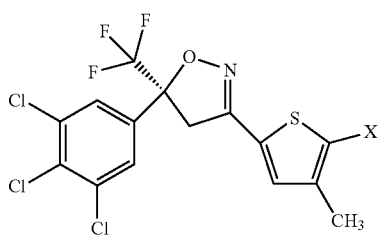

(ii) converting the bromide of compound of formula (4) to a carboxylic acid of the compound of formula (5)

(5)

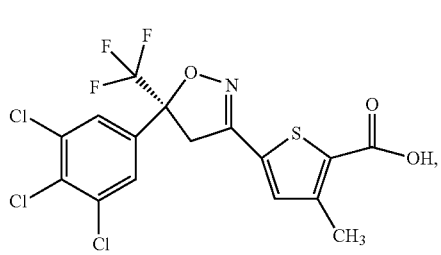

(iii) optionally crystallizing the compound of formula (5) with acetonitrile, and optionally with an anti-solvent selected from the group consisting of water and n-heptane, and (iv) coupling the compound of formula 5 with an amine, wherein the amine is a compound of formula (6), (6)

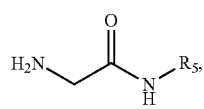

or glycine, optionally carboxyl protected;
wherein $R_5$ is a $C_1$-$C_4$ aliphatic chain, wherein the chain is optionally substituted with 1 to 5 halogen;
wherein the enantiomeric excess of the (S)-enantiomer of the compound of formula (1) is 90% or greater.

2. The process of claim 1, wherein the amine is 2-amino-2',2',2'-trifluoroethyl-acetamide,

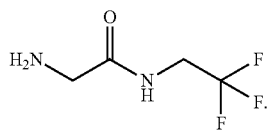

3. The process of claim 1, wherein the compound of formula (5) is reacted with glycine optionally carboxyl protected, followed by coupling with 2,2,2-trifluorethylamine.

4. The process of claim 1, wherein the reaction of the compound of formula (2) with hydroxylamine, sodium hydroxide, and a compound of formula (3) is conducted in the presence of a solvent system comprising dichloromethane and an ether.

5. The process of claim 1, wherein the enantiomeric excess of the compound of formula (5) is greater than or equal to 90%.

6. The process of claim 1, wherein (iii) crystallizing occurs.

7. The process of claim 6, wherein (iii) crystallizing occurs, and wherein the enantiomeric purity of the compound of formula (5) is 98% or greater.

8. The process of claim 7, wherein (iii) crystallizing occurs, wherein the solvent is acetonitrile, and wherein the enantiomeric purity of the compound of formula (5) is 98% or greater.

9. The process of claim 6, wherein the anti-solvent is present, wherein the anti-solvent is water.

10. The process of claim 1, wherein the compound of formula (3) is

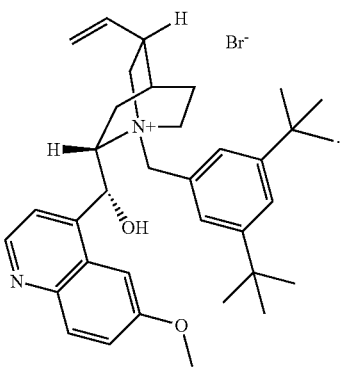 [SMILES: C=CC1C[N+]2(Cc3cc(C(C)(C)C)cc(C(C)(C)C)c3)CCC1C[C@H]2[C@H](O)c1ccnc2ccc(OC)cc12 ; [Br-]]

11. The process of claim 1, wherein the compound of formula (1) is (1)

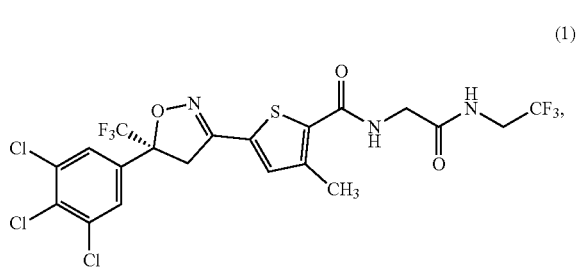 [SMILES: Cc1cc(C2=NO[C@@](c3cc(Cl)c(Cl)c(Cl)c3)(C(F)(F)F)C2)sc1C(=O)NCC(=O)NCC(F)(F)F]

wherein the process comprises:
(i) reacting a compound of formula (2)

(2)

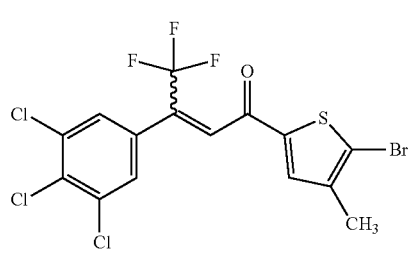

with hydroxylamine, sodium hydroxide and a compound of formula (3) in the presence of a solvent system comprising dichloromethane and an ether, (3)

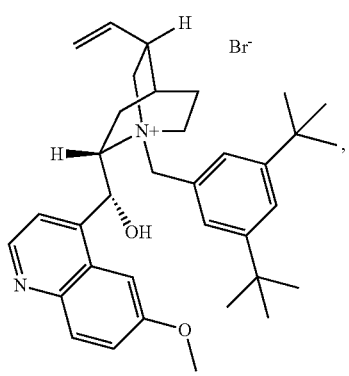

to give a compound of formula (4)

(4)

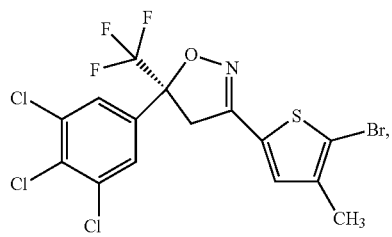

(ii) converting the bromide of compound of formula (4) to a carboxylic acid of the compound of formula (5)

(5)

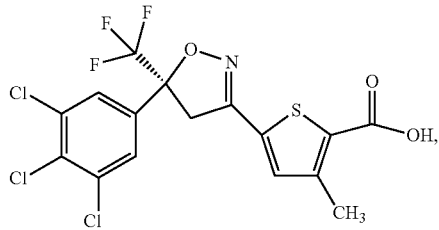

(iii) optionally crystallizing the compound of formula (5) with acetonitrile, and optionally with an anti-solvent selected from the group consisting of water and n-heptane,
and
(iv) coupling the compound of formula 5 with 2-amino-2',2',2'-trifluoroethyl-acetamide; wherein the enantiomeric excess of the(S)-enantiomer of the compound of formula (1) is 90% or greater.

12. The process of claim 11, wherein the enantiomeric excess of the compound of formula (5) is greater than or equal to 90%.

13. The process of claim 12, wherein (iii) crystallizing occurs.

14. The process of claim 10, wherein (iii) crystallizing occurs, and wherein the enantiomeric purity of the compound of formula (5) is 98% or greater.

15. The process of claim 14, wherein (iii) crystallizing occurs, wherein the solvent is acetonitrile, and wherein the enantiomeric purity of the compound of formula (5) is 98% or greater.

16. The process of claim 13, wherein the anti-solvent is present, wherein the anti-solvent is water.

17. The process of claim 1, wherein the compound of formula (1) is (1)

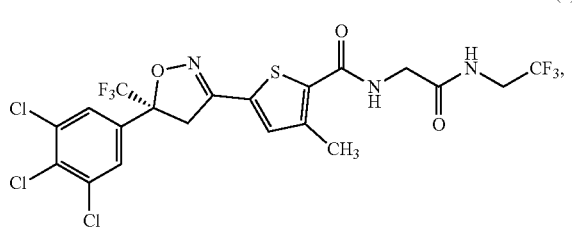

wherein the process consists essentially of:
(i) reacting a compound of formula (2)

(2)

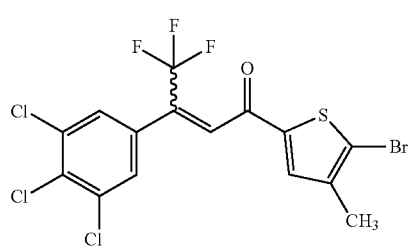

with hydroxylamine, sodium hydroxide and a compound of formula (3) in the presence of a solvent system comprising dichloromethane and an ether, (3)

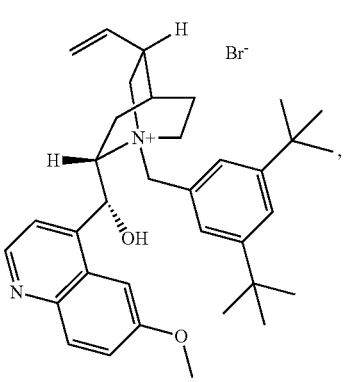

to give a compound of formula (4)

(4)

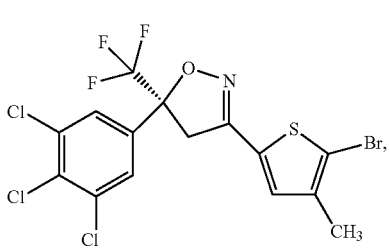

(ii) converting the bromide of compound of formula (4) to a carboxylic acid of the compound of formula (5)

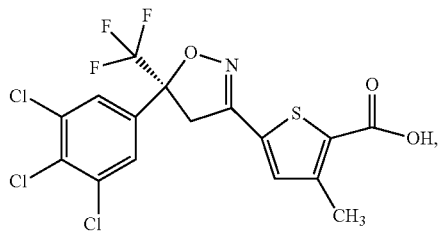
(5)

(iii) optionally crystallizing the compound of formula (5) with acetonitrile, and optionally with an anti-solvent selected from the group consisting of water and n-heptane, and (iv) coupling the compound of formula 5 with 2-amino-2',2',2'-trifluoroethyl-acetamide; wherein the enantiomeric excess of the(S)-enantiomer of the compound of formula (1) is 90% or greater.

18. The process of claim 17, wherein the enantiomeric excess of the compound of formula (5) is greater than or equal to 90%.

19. The process of claim 18, wherein (iii) crystallizing occurs.

20. The process of claim 19 wherein (iii) crystallizing occurs, and wherein the enantiomeric purity of the compound of formula (5) is 98% or greater.

21. The process of claim 20, wherein (iii) crystallizing occurs, wherein the solvent is acetonitrile, and wherein the enantiomeric purity of the compound of formula (5) is 98% or greater.

22. The process of claim 19, wherein the anti-solvent is present, wherein the anti-solvent is water.

23. The process of claim 1, wherein the compound of formula (1) is

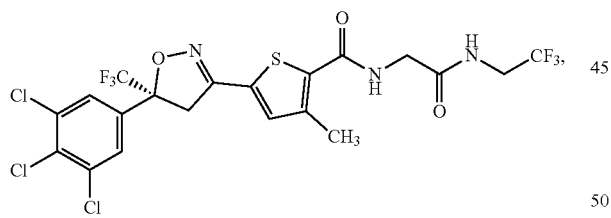
(1)

wherein the process consists of:
(i) reacting a compound of formula (2)

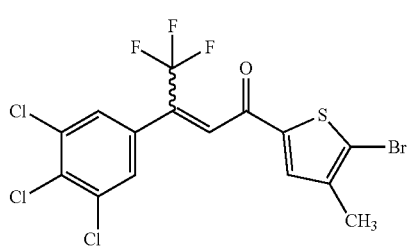
(2)

with hydroxylamine, sodium hydroxide and a compound of formula (3) in the presence of a solvent system comprising dichloromethane and an ether,

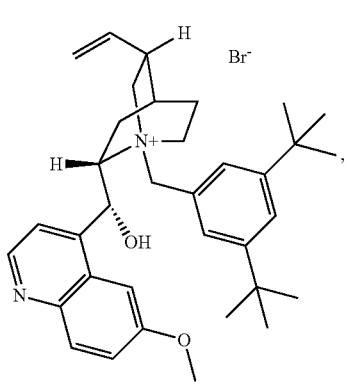
(3)

to give a compound of formula (4)

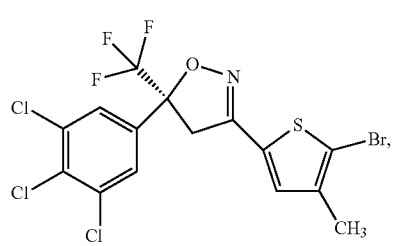
(4)

(ii) converting the bromide of compound of formula (4) to a carboxylic acid of the compound of formula (5)

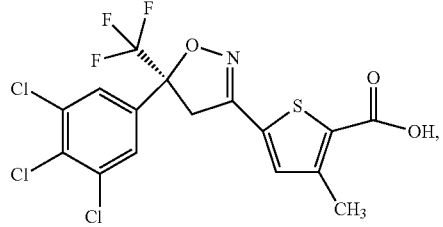
(5)

(iii) optionally crystallizing the compound of formula (5) with acetonitrile, acetone, ethanol, and tetrahydrofuran, and optionally with an anti-solvent selected from the group consisting of water and n-heptane, and (iv) coupling the compound of formula 5 with 2-amino-2',2',2'-trifluoroethyl-acetamide, wherein the enantiomeric excess of the(S)-enantiomer of the compound of formula (1) is 90% or greater.

24. The process of claim 23, wherein (iii) crystallizing occurs.

25. The process of claim 24, wherein (iii) crystallizing occurs, and wherein the enantiomeric purity of the compound of formula (5) is 98% or greater.

26. The process of claim 25, wherein (iii) crystallizing occurs, wherein the solvent is acetonitrile, and wherein the enantiomeric purity of the compound of formula (5) is 98% or greater.

27. The process of claim 24, wherein the anti-solvent is present, wherein the anti-solvent is water.

28. The process of claim 1, wherein $R_5$ is a $C_1$-$C_4$ aliphatic chain substituted with 1 to 5 halogen.

* * * * *